(12) United States Patent
Randhawa et al.

(10) Patent No.: US 10,692,596 B2
(45) Date of Patent: Jun. 23, 2020

(54) HEALTH KIOSK

(71) Applicant: Mobile NewMedia Ltd., Surrey (CA)

(72) Inventors: Tejinder S. Randhawa, Surrey (CA); John Richards, Port Coquitlam (CA)

(73) Assignee: Mobile NewMedia Ltd., Surrey (CA)

( * ) Notice: Subject to any disclaimer, the term of this patent is extended or adjusted under 35 U.S.C. 154(b) by 0 days.

(21) Appl. No.: 16/231,260

(22) Filed: Dec. 21, 2018

(65) Prior Publication Data

US 2019/0252060 A1  Aug. 15, 2019

Related U.S. Application Data

(63) Continuation of application No. 13/221,828, filed on Aug. 30, 2011, now Pat. No. 10,204,210.

(60) Provisional application No. 61/378,369, filed on Aug. 30, 2010.

(51) Int. Cl.

| G06F 15/16 | (2006.01) |
|---|---|
| G16H 30/20 | (2018.01) |
| G06F 19/00 | (2018.01) |
| H04L 12/24 | (2006.01) |
| H04L 29/08 | (2006.01) |
| H04W 8/22 | (2009.01) |
| H04L 29/06 | (2006.01) |
| G06F 16/95 | (2019.01) |
| G16H 10/60 | (2018.01) |

(52) U.S. Cl.
CPC .......... *G16H 30/20* (2018.01); *G06F 19/321* (2013.01); *G06F 16/95* (2019.01); *G16H 10/60* (2018.01); *H04L 41/0253* (2013.01); *H04L 63/0876* (2013.01); *H04L 67/30* (2013.01); *H04L 67/34* (2013.01); *H04W 8/22* (2013.01)

(58) Field of Classification Search
USPC .......................................................... 709/219
See application file for complete search history.

(56) References Cited

U.S. PATENT DOCUMENTS

| 5,497,421 | A | * | 3/1996 | Kaufman | G06F 21/335 |
|---|---|---|---|---|---|
| | | | | | 380/28 |
| 6,237,033 | B1 | | 5/2001 | Doeberl et al. | |
| 6,694,025 | B1 | * | 2/2004 | Epstein | H04L 9/083 |
| | | | | | 380/277 |

(Continued)

OTHER PUBLICATIONS

Kristol et al., RFC 2109 "HTTP State Management Mechanism", Feb. 1997, Network Working Group—RFC 2109, p. 1-20.

(Continued)

*Primary Examiner* — Taylor A Elfervig

(74) *Attorney, Agent, or Firm* — Todd A. Rattray; Oyen Wiggs Green & Mutala LLP

(57) ABSTRACT

A health kiosk system is provided. A kiosk has a computing unit and a physiological measurement apparatus connected to the computing unit. A Web browser of the computing unit transmits information corresponding to the physiological measurement apparatus and a request for a resource to a Web server. In response to receiving the request, the Web server transmits to the kiosk profile-specific Web content responsive to the request and specific to the received profile information. The information corresponding to the physiological measurement apparatus may be transmitted in a URL or HTTP Cookie of an HTTP request.

20 Claims, 7 Drawing Sheets

(56) References Cited

U.S. PATENT DOCUMENTS

| | | | |
|---|---|---|---|
| 7,039,810 B1 * | 5/2006 | Nichols | G06F 19/3418 |
| | | | 713/182 |
| 2002/0116550 A1 | 8/2002 | Hansen | |
| 2002/0183599 A1 | 12/2002 | Castellanos | |
| 2003/0061487 A1 * | 3/2003 | Angelo | G06F 21/565 |
| | | | 713/176 |
| 2004/0044560 A1 | 3/2004 | Giglio et al. | |
| 2008/0177796 A1 | 7/2008 | Eldering | |
| 2009/0275844 A1 | 11/2009 | Al-Ali | |
| 2010/0161394 A1 | 6/2010 | Bell et al. | |
| 2010/0318578 A1 | 12/2010 | Treu et al. | |
| 2011/0161951 A1 | 6/2011 | Anderson | |
| 2011/0282168 A1 * | 11/2011 | Weiss | A61B 5/742 |
| | | | 600/323 |
| 2012/0017149 A1 | 1/2012 | Lai et al. | |

OTHER PUBLICATIONS

Tia Gao D. Greenspan, M. Walsh, R. R. Juang and A. Alm, "Vital Signs Monitoring and Patient Tracking Over a Wireless Network," 2005 IEEE Engineering in Medicine and Biology 27th Annual Conference, Shanghai, 2005, pp. 102-105, (Year; 2005).

F. Rahman, A. Kumar, G. Nagendra and G.S. Gupta, "Network approach for physiological parameters measurement," in IEEE Transactions on Instrumentation and Measurement, vol. 54, No. 1, pp. 337-346, Feb. 2005, (Year: 2005).

\* cited by examiner

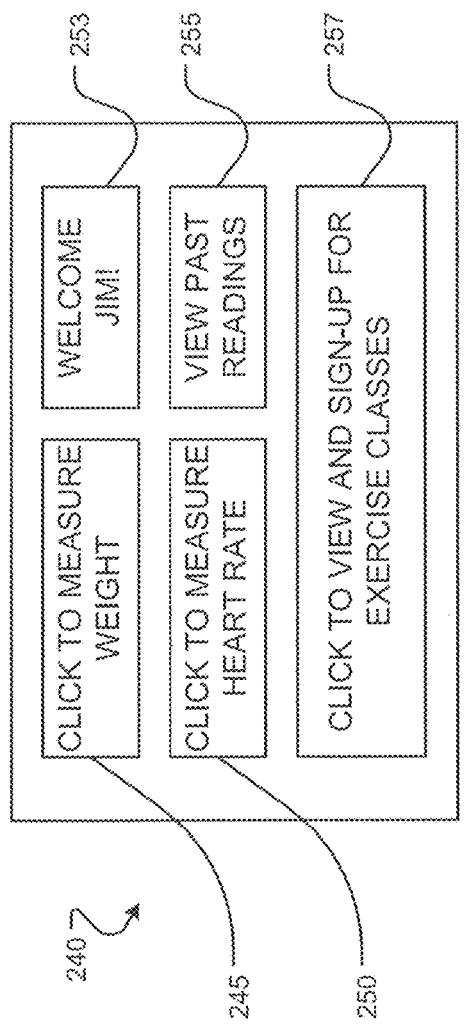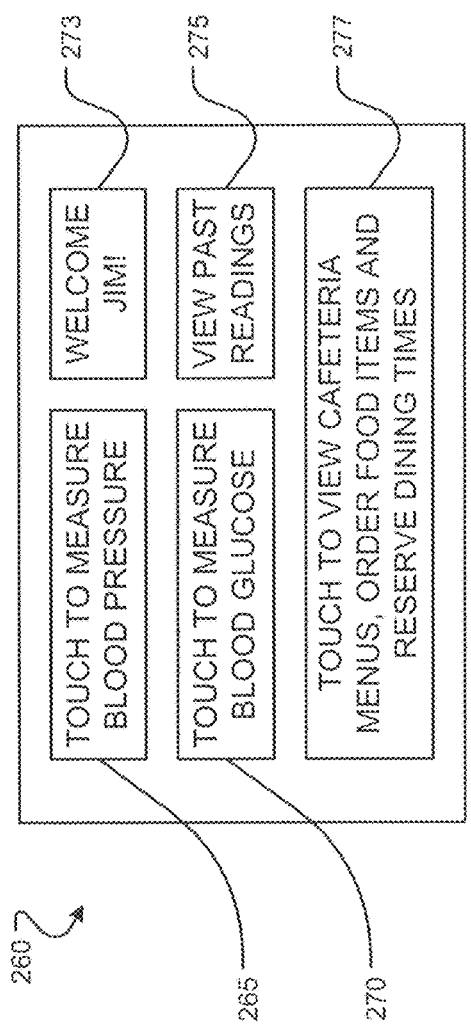
FIGURE 5A
FIGURE 5B

HEALTH KIOSK

CROSS-REFERENCE TO RELATED APPLICATION

This application is a continuation of application Ser. No. 13/221,828 filed 30 Aug. 2011, and entitled "Health Kiosk", which claims the benefit under 35 U.S.C. § 119 of application Nos. 61/378,369 filed on 30 Aug. 2010 and entitled "Health Kiosk". Both application Ser. Nos. 13/221,828 and 61/378,369 are hereby incorporated herein by reference for all purposes.

TECHNICAL FIELD

The invention pertains to kiosks which may be used by human subjects to obtain measurements of physiological parameters. Particular embodiments provide a client-server kiosk architecture by which a plurality of diversely configured kiosks may be centrally administered by a server.

BACKGROUND

It is now common for the elderly to live in managed care facilities that provide supportive environments to ease the burdens of aging. There is an increasing interest in monitoring the health of residents at such care facilities. In addition to the elderly themselves, loved ones, government authorities and insurers may each have an interest in the continued health of resident of managed care facilities.

Health kiosks installed in such facilities may be used to measure and monitor indicators of the health of facility residents. Some kiosks are connected to communication networks, and can interact with remote computing facilities. Prior art health kiosks may suffer from one or more of the following disadvantages:
- difficulty in installing the kiosks;
- difficulty in adding additional physiological measurement apparatus to kiosks;
- difficulty in establishing a unique identifier for the kiosk;
- difficulty in managing, storing and transmitting health data to interested parties;
- difficulty in providing health data that can be authenticated and/or verified;
- difficulty in providing communication connectivity outside the local area network due to firewalls and the like;
- difficulty in administering differently configured kiosks;
- inadequate means for motivating residents to interact with the kiosks;
- inadequate provisions for preserving resident privacy; and
- prohibitive financial cost.

Health kiosks may also find application in myriad other locations, including without limitation, fitness centers, community centers, physicians offices, long term care facilities, public health offices, and the like.

The foregoing examples of the related art and limitations related thereto are intended to be illustrative and not exclusive. Other limitations of the related art will become apparent to those of skill in the art upon a reading of the specification and a study of the drawings.

SUMMARY

One aspect of the invention provides a health kiosk system comprising a server having a Web server, a kiosk communicatively coupled to the server, the kiosk comprising a computing unit, at least one physiological measurement apparatus connected to the computing unit, and a display. The computing unit has a Web browser configured to transmit profile information indicative of a profile of the kiosk to the Web server, the profile comprising information corresponding to the at least one physiological measurement apparatus, and to transmit a request for a resource to the Web server. The Web server is configured to, in response to receiving the profile information and the request, transmit to the kiosk profile-specific Web content responsive to the request and based at least in part on the profile information.

Another aspect of the invention provides a health kiosk comprising a computing unit, a display and at least one physiological measurement apparatus connected to the computing unit. The computing unit has a Web browser configured to transmit profile information indicative of a profile of the kiosk to a particular Web server, the profile comprising information corresponding to the at least one physiological measurement apparatus, to transmit a request for a resource to the particular Web server, and to render Web content received in response to the request for display on the display. The particular Web server may be predetermined as part of the configuration of the kiosk.

A further aspect of the invention provides method in a health kiosk system including kiosk having at least one physiological measurement apparatus and a server. The method comprises transmitting from the kiosk to the server profile information indicative of a profile of the kiosk, the profile comprising information corresponding to the at least one physiological measurement apparatus, transmitting from the kiosk to the server a request for a resource, and, in response to receiving the request, transmitting from the server to the kiosk profile-specific Web content responsive to the request and based at least in part on the profile information.

Yet another aspect of the invention provides a non-transitory computer readable medium comprising a computer program product having code that when executed by a computing unit causes the computing unit of a kiosk to transmit profile information indicative of a profile of the kiosk to a server, the profile comprising information corresponding to at least one physiological measurement apparatus of the kiosk, and to transmit a request for a resource to the server.

BRIEF DESCRIPTION OF DRAWINGS

Exemplary embodiments are illustrated in referenced figures of the drawings. It is intended that the embodiments and figures disclosed herein are to be considered illustrative rather than restrictive.

FIG. A is a diagram of inter-process communication in a health kiosk system according to an example embodiment.

Figure 2:
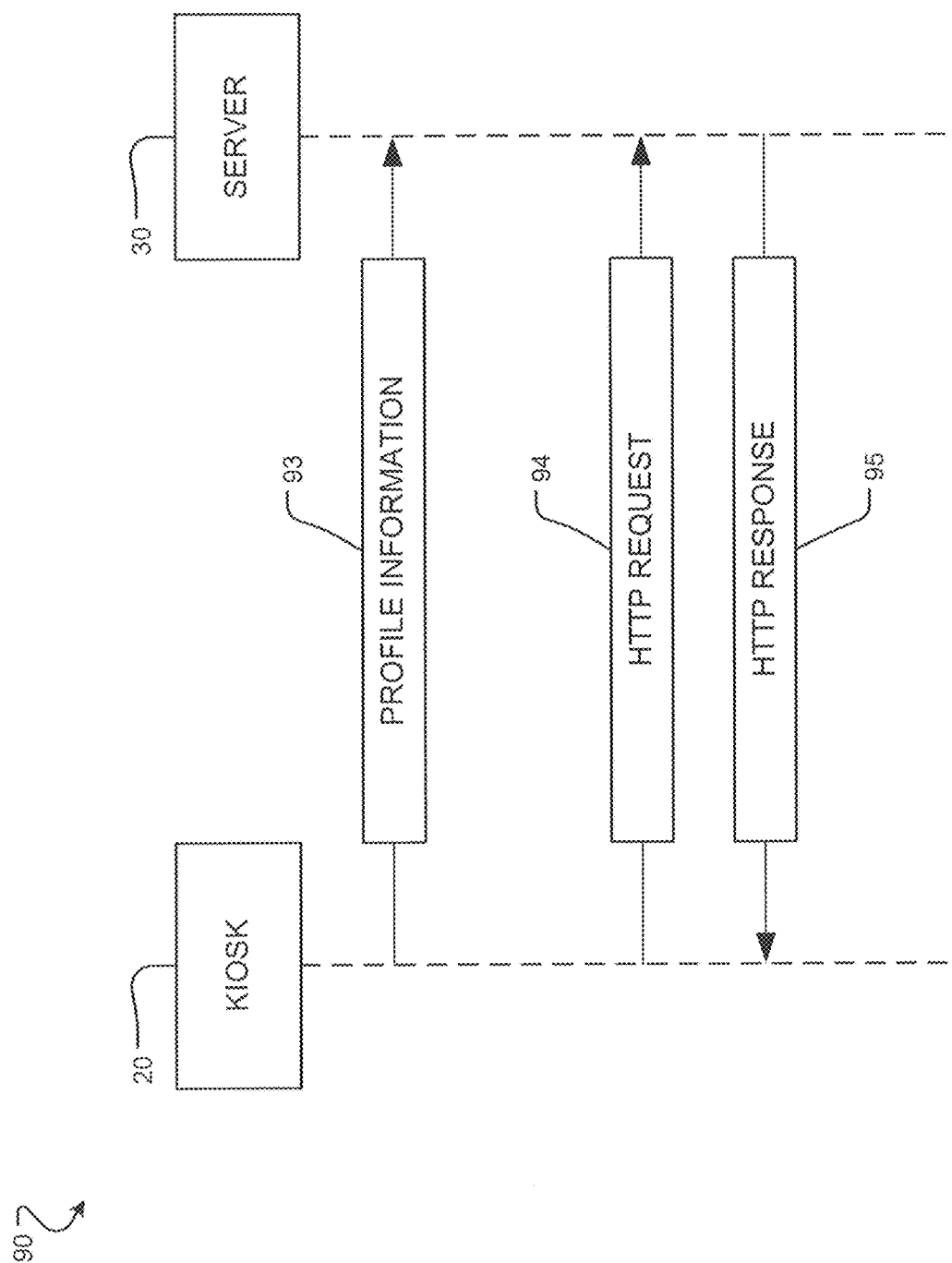

FIG. 2 is a communication diagram of a method in a health kiosk system according to an example embodiment.

Figure 3:
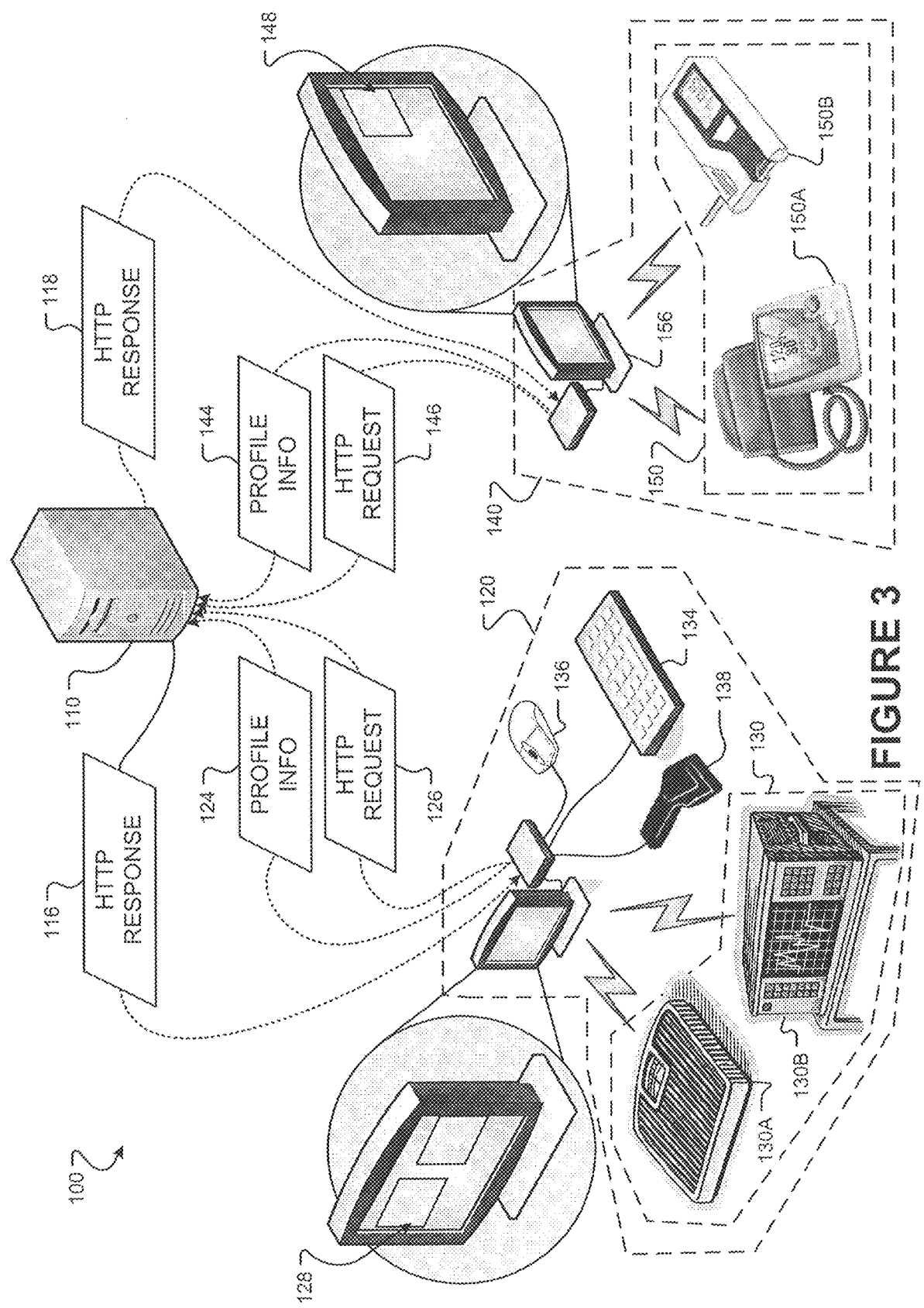

FIG. 3 is a diagram of a health kiosk system according to an example embodiment.

FIGS. 4A-5B are diagrams representing renderings of Web content provided from a server to kiosk in an example embodiment.

Figure 6:
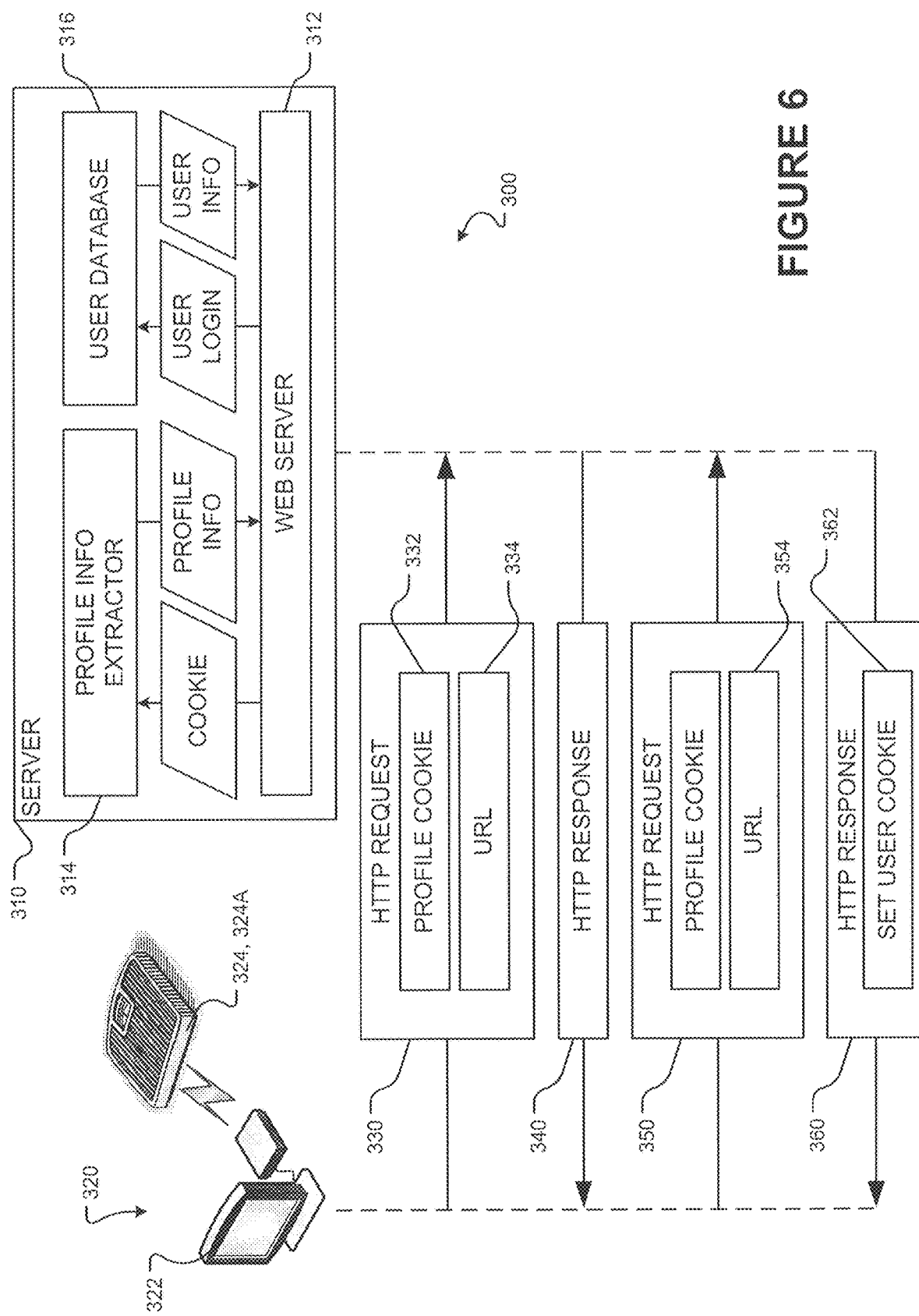

FIG. 6 is a diagram of a health kiosk system according to an example embodiment.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Figure 1:
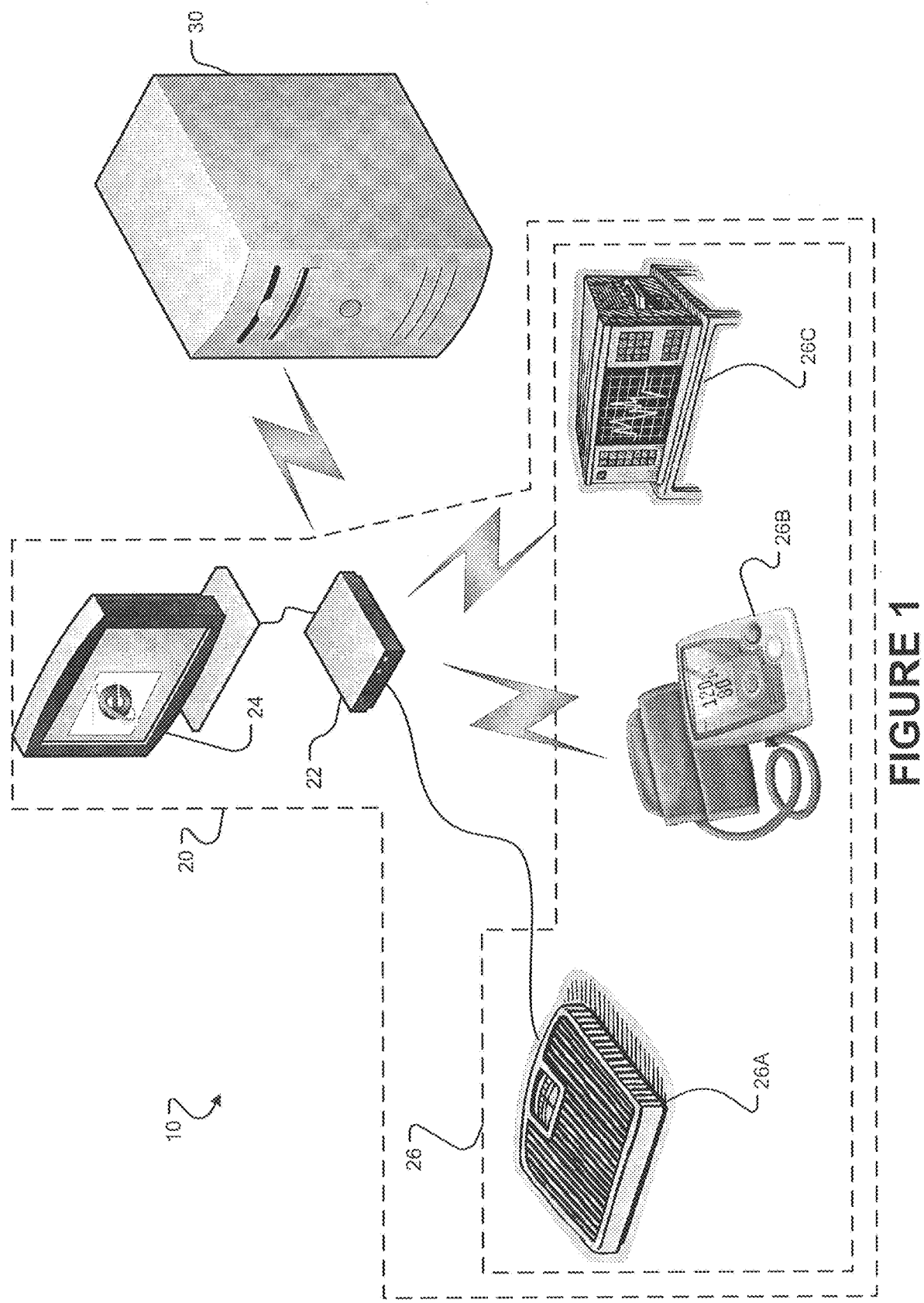
FIG. 1 is a diagram of a health kiosk system according to an example embodiment.

FIG. 1 is a diagram of a health kiosk system 10 according to an example embodiment. A client health kiosk 20 is communicatively coupled to a server 30. Kiosk 20 may be communicatively coupled to server 30 by one or more electronic networks, such as a local area network (e.g., an Ethernet network), a wide area network (e.g., the Internet), or the like. Kiosk 20 may be directly connected to server 30. Server 30 may be geographically remote from client health kiosk 20. Kiosk 20 may be one of a number of client health kiosks communicatively coupled to server 30.

Kiosk 20 comprises a computing unit 22 coupled to a display 24. Computing unit 22 may comprise a personal computer, an embedded computing appliance, or the like. In the illustrated embodiment, computing unit 22 comprises a network communications interface (not shown), by which computing unit 22 may connect to a communication network. Those skilled in the art will appreciate that with an appropriate network interface, computing unit 22 can connect to any of a wide variety of communication networks, such as, for example wired and/or wireless local area networks, wireless wide area networks, or the like.

Display 24 may comprise any suitable display, such as, for example, an liquid crystal display (LCD), a cathode ray tube (CRT) display, a television, or the like. In the illustrated embodiment, display 24 comprises a touch screen input interface. Other embodiments may provide alternative and/or supplementary user interface input apparatus, such as, for example, a keyboard, a mouse, a trackball, a microphone, a stylus and touch pad, and the like. Other embodiments may provide alternative and/or supplementary user interface output apparatus, such as, for example, audio speakers, headphones, signaling lamps, and the like. Some embodiments comprise apparatus for receiving input to identify users of the kiosk, such as, for example, a magnetic card reader, a bar code scanner, a microphone for voice recognition, a camera for face recognition, a thumb/fingerprint scanner, wireless communication means (e.g., RFID tag readers, Bluetooth transceiver, WiFi transceivers, etc.), and the like. In some embodiments, computing unit 22 and display 24 are integrated into a single enclosure.

Kiosk 20 also comprises one or more physiological measurement apparatus. In the illustrated embodiment, kiosk 20 comprises a weight scale 26A, a portable blood pressure monitor 26B, and a heart rate monitor 26C (collectively, physiological measurement apparatus 26). Physiological measurement apparatus are operatively coupled to computing unit 22 via suitable interfaces. Such interfaces may comprise standardized device interfaces, such as, for example, USB interfaces, serial port interface, Bluetooth interfaces, WiFi interfaces, and the like. Operative couplings between computing unit 22 and physiological measurement apparatus 26 may comprise wired and/or wireless links.

Computing unit 22 is operable to acquire physiological measurements of a human subject obtained by physiological measurement apparatus 26. In some embodiments computing unit 22 is operable to obtain physiological measurement data from two or more physiological measurement apparatus 26 at the same time. For example two or more blood pressure monitors may be connected to computing unit 22, and computing unit 22 may be operable to simultaneously receive, store and/or display data from each such blood pressure monitor.

In some embodiments, kiosk 20 is configurable such that physiological measurement apparatus 26 may be added, removed and/or interchanged. Other physiological measurement apparatus 26 that may be incorporated into various embodiments of kiosk 20 include, without limitation, blood pressure cuffs, pulseoxymeters, EKGs, ECGs, blood glucose meters, thermometers, and the like. In some embodiments, kiosk 20 comprises a plurality of the same type of physiological measurement apparatus 26. Those skilled in the art will appreciate that computing unit 22 may be coupled to virtually any physiological measurement apparatus 26 having a suitable interface, and it is intended that the illustrated embodiment not be understood as limited to the illustrated or currently known physiological measurement apparatus 26. Kiosk 20 may be provided without physiological measurement apparatus 26 (i.e., kiosk 20 and physiological measurement apparatus 26 may be provided separately).

Server 30 is configured to run a Web server (not shown in FIG. 1) and applications, including without limitation, a database server (not shown). The database server may be configured to store and retrieve data pertaining to users of client health kiosks 20, such as physiological measurement data, for example. It will be appreciated that all or part of the data available to the database server on server 30 may be located in a data store remote from server 30.

The Web server of server 30 may be configured to communicate data using the HTTP protocol. Data communicated by the Web server of server 30 may comprise Web content including, without limitation, content that may be rendered by a Web browser (e.g., content embodied in HTML, CSS, Javascript and/or other Web languages), content that may be embedded in Web pages (e.g., images, videos, audio, etc.), and client-side executable content configured to run in a Web browser (e.g., plug-ins, applets, ActiveX controls, etc.), and the like. Server 30 may be configured to run other servers capable of communicating data using protocols other than HTTP. Server 30 may be configured to choose one or more protocols for communicating data based, at least in part, on the presence or absence of intermediary network firewalls that block particular types of network traffic, and/or on the data throughput supported by one or more of the connections between kiosk 20 and server 30 (for instance, low-throughput General Packet Radio Service (GPRS) connections).

As is understood in the art, Web browsers are operable to communicate with Web servers using the hypertext transport protocol (HTTP). HTTP is a request-response protocol standard for client-server computing. In HTTP, a Web browser, for example, acts as a client, while a Web server acts as a server. Web browsers generate and transmit HTTP requests to request information from resources identified in the HTTP request. Web servers, which store and/or have access to resources, send HTTP responses back to Web browsers in response to HTTP requests. These returned messages may contain the resource requested by the client and/or other kinds of response indications.

Resources provided by Web servers may be identified using Uniform Resource Locators (URLs). A URL is a textual descriptor that typically consists of a hostname (alternatively, an IP address) that identifies the Web server to which the request is directed and a path to a resource to be fetched or a program to be run on that Web server. Optionally, a URL may contain a port number that specifies a non-standard port on the Web server to which the request should be directed and/or a query string that contains arguments for a program to be run. In some HTTP requests, the hostname (and, optionally, the port number) is specified in a Host header field and the path (and, optionally, the query string) is specified in a Request line.

Computing unit 22 of kiosk 20 may be configured to run a Web browser capable of requesting, receiving and rendering Web content from server 30 on display 24. For example, kiosk 20 may be configured to run the Internet Explorer™ Web browser from Microsoft of Redmond Wash. Other Web browsers may be used. Kiosk 20 may be configured to request and/or receive data other than Web content. Kiosk 20 may be configured to request and/or receive data using protocols other than HTTP.

The Web browser of kiosk 20 is configured to generate an HTTP request that comprises a hostname or IP address identifying the Web server of server 30. In some embodiments, the Web browser of kiosk 20 is configured so that the URL of its default or home page identifies a resource at the Web server of server 30. In such embodiments, when the Web browser of kiosk 20 is initially loaded (e.g., when kiosk 20 is powered on), the Web content initially presented by kiosk 20 is that provided by server 30. Kiosk 20 may be configured so that, in typical operation (e.g., without administrator privileges), users may operate kiosk 20 only through content (e.g., links) provided in Web content displayed in the Web browser (i.e., kiosk 20 may be configured so that a user may access the Web browser, but no other functions of kiosk 20 except those made available through Web content from server 30 that is displayed in the Web browser).

In some embodiments, kiosk 20 is configured to communicate only with server 30. For example, kiosk 20 may comprise a firewall configured to allow inbound communication from server 30 only, and to allow outbound communication to server 30 only. In some embodiments, kiosk 20 and server 30 are configured for secure communication. For example, the secure Hypertext Transport Protocol (HTTP) may be used for communications between kiosk 20 and server 30.

Web content provided by the Web server of server 30 and rendered on the Web browser of kiosk 20 may be configured to provide a user interface for operating kiosk 20 to do one or more of the following non-limiting example activities:
- taking measurements using physiological measurement apparatus 26 of kiosk 20;
- obtaining instructions/tutorials for using physiological measurement apparatus 26 of kiosk 20, in video, graphic, textual and/or audible formats;
- obtaining health information and advice in video, graphic, textual and/or audible formats;
- obtaining historical measurements of physiological parameters (e.g., measurements of physiological parameters obtained using physiological measurement apparatus 26 of kiosk 20, etc.);
- obtaining information about events, activities and the like occurring in the user's environment (e.g., calendars of activities at a care home, etc.);
- transmitting health information to physicians, loved ones, and other interested parties;
- collecting information about users by collecting responses to questions, including questions related to:
  - activities performed prior to kiosk use;
  - foods and drinks ingested prior to kiosk use;
  - medications ingested prior to kiosk use;
  - self-assessments of health;
  - self-assessments of stress level; and/or
  - the like; and/or
- the like.

In some embodiments, server 30 is configured to provide Web content that when rendered by kiosk 20, causes and/or enables kiosk 20 to transmit information collected at kiosk 20 (e.g., physiological measurements, responses to questions etc.) to server 30.

In some embodiments, server 30 is configured to provide client-side executable elements to kiosk 20, such as, for example Java applets, ActiveX controls and the like. Client-side executable elements may be configured to run within the Web browser or run on computing unit 22 outside of the Web browser. Client-side executable elements may be configured to interact with physiological measurement apparatus 26 of kiosk 20, such as to obtain physiological measurement data from, obtain apparatus status information about, and control the operation of physiological measurement apparatus 26, for example.

In some embodiments, Web content provided by the Web server of server 30, when rendered by the Web browser, provides controls for interfacing with apparatus connected to kiosk 20, such as, for example, user interface apparatus (e.g., display 24), user identification apparatus (not shown), and physiological measurement apparatus 26. For example, the Web server of server 30 may provide Web content that when rendered by the Web browser of kiosk 20 provides Javascript elements (e.g., command buttons, radio buttons, check boxes, list boxes, sliders, spinners, etc.) that when operated by a user cause Javascript code to be executed which invokes methods on ActiveX objects that have been instantiated and are hosted within the Web browser. The ActiveX objects may establish inter-process communication with one or more processes that interface with apparatus connected to kiosk 20. Inter-process communication may take the form of point-to-point message queues, window message, local TCP/IP socket connections, and the like. Through inter-process communications, ActiveX objects may be used to obtain physiological measurement data from, obtain apparatus status information about, and/or control the operation of physiological measurement apparatus 26, for example. Javascript elements rendered by the Web browser may be configured to display information regarding the use and/or state of apparatus connected to kiosk 20.

Figure 1A:
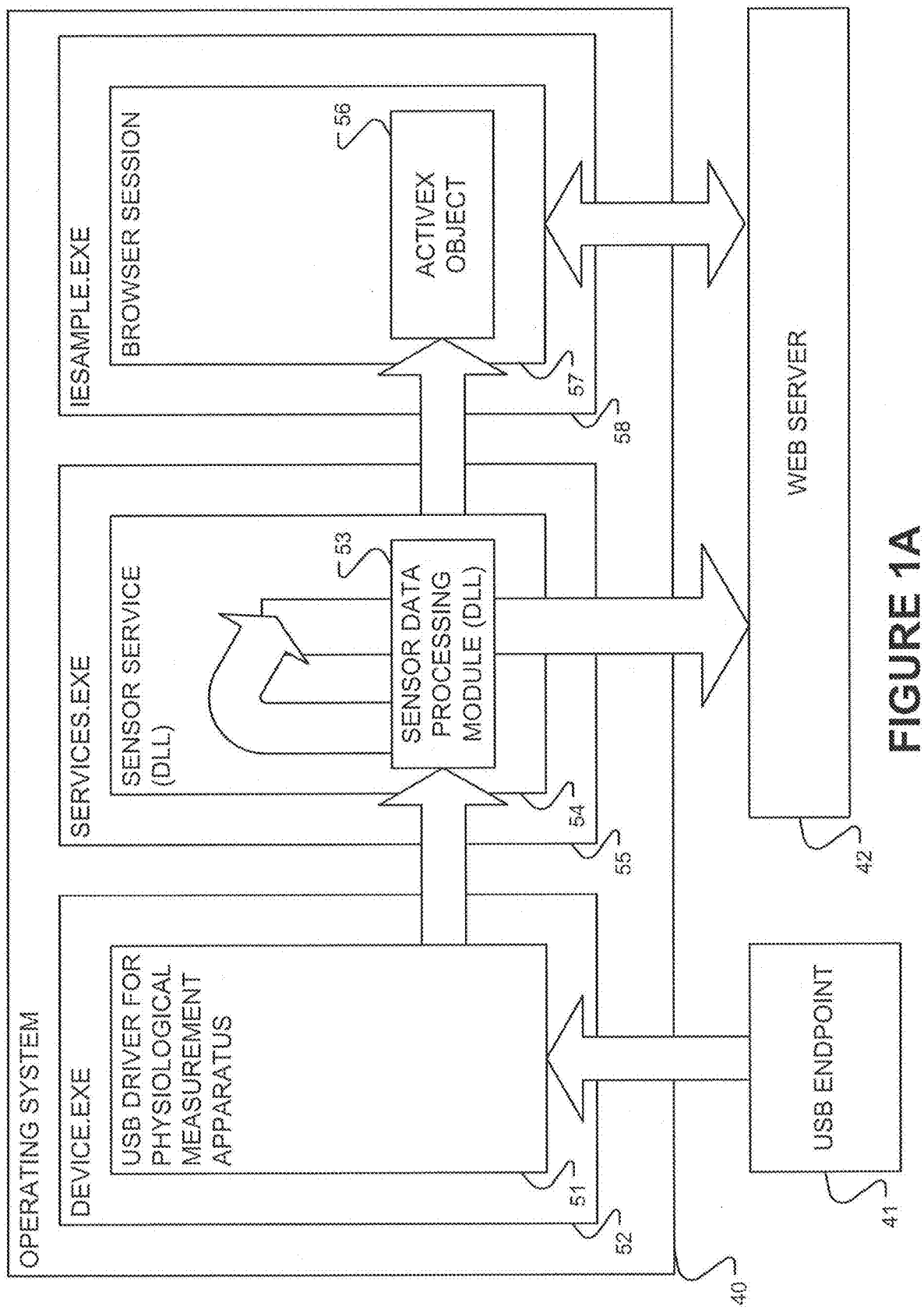

FIG. A is a diagram of inter-process communication according to an example embodiment in system 10 among processes running in the operating system 40 of kiosk 20, a USB endpoint 41 located in one of physiological measurement apparatus 26 (e.g., scale 26A), and the Web server 42 running on server 30. In FIG. 1A, physiological measurement sensor output is communicated from USB endpoint 41 to a USB driver 51 for scale 26A. USB driver 51 may be particular to a particular one of physiological measurement apparatus 26 (e.g., scale 26A in the case of the illustrated embodiment). USB driver 51 is hosted in the device.exe process 52 running on operating system 40 of computing unit 22. USB driver 51 transmits the physiological measurement sensor output to a sensor data processing module (DLL) 53.

Sensor data processing module 53 is loaded at runtime by a Sensor service (DLL) 54. Sensor service 54 is configured to load and coordinate various plugin modules (e.g., sensor data processing module(s) 53) and to manage the transmission of physiological measurement data to remote network recipient(s). Sensor service 54 may be particular to one or more of physiological measurement apparatus 26 (e.g., scale 26A in the case of the illustrated embodiment). Sensor service 54 is hosted within the services.exe process 55. Sensor data processing module 53 extracts physiological measurement data from the physiological measurement sensor output and submits this data to sensor service 54 for transmission to an ActiveX object 56 hosted within a browser session 57 of the iesample.exe process 58. Sensor data processing module 53 may be particular to one or more of physiological measurement apparatus 26 (e.g., scale 26A in the case of the illustrated embodiment). In some embodiments, ActiveX object 56 solicits physiological measurement data from sensor data processing modules 53. Such solicitation may occur directly, or be mediated by sensor service 54. ActiveX object 56 may be particular to one or more of physiological measurement apparatus 26 (e.g., scale 26A in the case of the illustrated embodiment).

ActiveX object 56 renders the physiological measurement data within the browser session 57 within which it is hosted. Browser session 57 may also receive physiological measurement data from Web server 42, and render it alongside a locally generated rendering of data received from sensor data processing module 53. For instance, ActiveX object 56 may render values of instantaneous pulse rate in real-time, while the browser session retrieves and renders historical pulse rate data from Web server 42. In some embodiments, system 10 is configured so that computationally expensive operations involving large data sets and extensive graphics computations may be performed on server 30, and computationally inexpensive operations involving small data sets may be performed in kiosk 20. In some embodiments, local data rendering may be employed for data requiring responsive operation (e.g., real time data) whereas remotely generated data may be employed for data whose display is less likely to be affected by network outages and delays.

In the illustrated embodiment, sensor service 54 also encapsulates the physiological measurement data for transmission to central Web server 42. Sensor Service 54 may be configured to encapsulate physiological measurement data in UDP datagram packets, TCP datagram packets, HTTP payloads, or the like.

It will be appreciated that in addition to or as an alternative to ActiveX object 56, controls may be embedded in Web content provided by Web server of server 30 and rendered by the Web browser of kiosk 20 using other protocols, such as, for example Java, Google Native Client, Adobe Flash, Silverlight, HTML5.

In some embodiments, server 30 is configured to store user information (e.g., physiological measurements) in encrypted form. For example, server 30 may be configured to maintain one or more cryptographic keys for a user, and to use such keys to encrypt user information. In some embodiments, server 30 is configured to maintain a record for each user that comprises a personal identifier (pid), a hash of the user's password (H(pwd)), personal information about the user (e.g., name, etc.), a public cryptographic key ($Pb_{user}$) for the user and private cryptographic key ($Pr_{user}$) for the user. In some embodiments, one or more of the elements of this record are stored in encrypted form. For example, server 30 may be configured to maintain a record having the following form for a user:

<pid, H(pwd), {name, personal information}$K_{user}$, {$Pr_{user}$}$K_{user}$,{$Pb_{user}$}$K_{server}$>

Where the notation "{x}y" denotes information "x" encrypted using the cryptographic key "y", and where $K_{user}$ is a secret cryptographic user key generated by server 30 from the user's password (pwd) and $K_{server}$ is secret cryptographic server key. Those skilled in the art will appreciate that when a user provides a username and password to log in, the input name may be used to look up a pid, and a hash of the input password checked against the stored hash of the password on record. Given the correct password, server 30 may generate $K_{user}$ and thereby decrypt $Pr_{user}$ for use in decrypting measurements signed with $Pb_{user}$.

In some applications, it is desirable that the integrity of physiological measurements and user information collected at kiosk 20 be verifiable. For example, where physiological measurements of users are used to monitor the performance of health care providers, it may be important that the data collected by kiosk 20 not be falsified, tampered with or manipulated. In some embodiments, server 30 is configured to use cryptography to digitally sign physiological measurements and the like provided from kiosk 20. Server 30 may be configured to generate a digital signature for the record by calculating a hash of the record and encrypting the hash value using the user's private key. The encrypted hash value may then be stored along with the record for subsequent authentication of the record. Authentication may be performed by computing a hash value for the stored record and comparing it with the hash value recovered by decrypting the encrypted hash value using the user's public key. Advantageously, where the user's private key is only accessible to the user (e.g., where it is generated from a secret password known only to the user), the use of private key encryption may provide assurance that the user was in fact present when a physiological measurement was taken.

In some embodiments, server 30 is configured to store physiological measurements and corroborative information which may be used to audit the physiological measurements. Corroborative information may include, for example:

an identifier of the particular kiosk at which the measurement was obtained;
the type of equipment that obtained the measurement;
an identifier of the particular equipment used to obtain the measurement (e.g., serial number);
a timestamp of when the measurement was received at the server;
a timestamp of when the user logged into the kiosk;
a timestamp of when the user logged out of the kiosk; and the like.

Physiological measurements and corroborative information may be stored as part of the same encrypted and/or digitally signed record to ensure integrity and permit subsequent authentication.

In some embodiments, temporally-specific symmetric session keys are used to sign records. As compared to RSA private user keys, signing records using temporally specific session keys may require less computing overhead. In some embodiments, records are signed using session keys that are temporally-specific and user-specific, and the session keys are encrypted with the user's private key for storage (e.g., keys are stored as part of a record in the form <pid, timePeriod, {$K_{SESSION}(timePeriod)$}$Pr_{user}$>), where pid is an unique identifier of the user, timePeriod refers to a defined period of time, $K_{SESSION}(timePeriod)$ is a session key for the period of time identified by timePeriod and $Pr_{user}$ is the user's private key.

In some embodiments, multiple, differently configured kiosks 20 are in communication with server 30. Kiosks 20 may differ among one another in one or more of the following example aspects of configuration:

physiological measurement apparatus;
operational characteristics and/or states of physiological measurement apparatus (e.g., battery power levels, on/off states, etc.);
display properties (e.g., colors, resolution, size, etc.);
user interface apparatus (e.g., voice recognition apparatus, keyboard, mouse, touch screen, speakers, printers, etc.);

user identification apparatus (e.g., bar code scanners, RFID scanners, magnetic card readers, biometric identification apparatus, etc.);

computing capability (e.g., hardware (RAM, storage, processor type and speed, availability of onboad math coprocessor, etc.) and software (operating system and version thereof, Web browser and version thereof, installed audio and video codecs, etc.));

network connectivity (e.g., wireless, wired, LAN, WAN, physical, media access and link layer properties); and the like.

Kiosks 20 may be characterized by one or more logical affiliations. Kiosks 20 connected to a given server 30 may differ among one another in one or more of the example logical affiliations:

geographic location;
institution/facility;
health care provider;
governmental health region/supervising regulatory agency;
health insurer;
target demographic (e.g., by gender, age, general health condition, language, cognitive ability, etc.);
local physical surroundings (e.g, cafeteria, exercise facility, lounge, nursing station);
advertising network;
associated incentive programs;
globally unique identifier; and
the like.

Aspects of configuration and/or logical affiliations that characterize a kiosk 20 may be combined to form a profile that is characteristic of the kiosk. As used herein, the term "profile" denotes a combination of configuration information and/or affiliation information that is characteristic of a kiosk 20. A single kiosk 20 may have several different profiles, each profile corresponding to a different set of configuration aspects and logical affiliations.

In some embodiments, kiosk 20 is configured to maintain profile information about itself in one or more local datastores. Profile information maintained in a local datastore may be obtained manually (e.g., programmed by a technician, input by a user, etc.), automatically (e.g., by a background process that continuously monitors the configuration of kiosk 20, a global positions system receiver, etc.) or through a combination thereof. As used herein the term "profile information" refers to information indicative of the profile of the kiosk (e.g., indicating and/or specifying one or more aspects of configuration, logical affiliation or combination thereof that is characteristic of a kiosk 20). Profile information may include, without limitation, configuration information (e.g., information corresponding to physiological measurement apparatus, user identification apparatus, etc.), logical affiliation information (e.g., information corresponding to institution, health care provider, local physical surroundings, etc.), and other information that is associated with the profile of a kiosk 20.

In some embodiments, kiosk 20 is configured to transmit profile information to server 30 before and/or with an HTTP request to server 30. In some embodiments, server 30 is configured to receive the profile information and provide Web content to kiosk 20 that is customized for the particular profile of kiosk 20. Web content customized for a particular profile may include Web content that when rendered by the Web browser of kiosk 20 and displayed on display 24 provides a customized user interface for operating kiosk 20.

FIG. 2 is a communication diagram of a method 90 according to an example embodiment. In block 93, a kiosk 20 transmits profile information to a server 30. In block 94, kiosk 20 transmits an HTTP request comprising a URL that identifies a resource at server 30. Based on information conveyed in the block 94 HTTP request, server 30 associates the block 94 HTTP request with the block 93 profile information. In block 95, server 30 transmits an HTTP response to kiosk 20, which contains Web content determined by server 30 based on the URL contained in the block 94 HTTP request and the block 93 profile information of kiosk 20. In some embodiments, block 93 and block 94 are combined. For example, an HTTP request may comprise profile information and a URL.

In some embodiments, kiosk 20 is configured to transmit profile information in the form of a profile identifier. A profile identifier comprises a value (e.g., string, number, etc.) indicative of profile information. A profile identifier may comprise a global unique identifier (GUID) that is uniquely associated with a kiosk. A profile identifier may be associated with profile information by a look-up table, a computable function, or the like, for example. A profile identifier may be determined from profile information using a look-up table, a computable function, or the like, for example. Server 30 and kiosk 20 may be configured to associate profile information with profile identifiers according to a common scheme.

A profile identifier may be determined for kiosk 20 locally by manual means (e.g., by a technician who inputs a profile identifier value obtained from a look-up table, a computable function that takes profile information as input, or the like) or automatically (e.g., kiosk 20 may be configured to generate a profile identifier using a computable function that takes profile information as input, a lookup table, or the like).

In some embodiments, kiosk 20 may be configured to obtain a profile identifier indicative of a profile of kiosk 20 from server 30. For example, server 30 may be configured to generate and transmit a profile identifier to kiosk 20 based on profile information transmitted from kiosk 20. In some embodiments, server 30 is configured to determine a profile identifier based on profile information using a computable function, a lookup table or the like. In some embodiments, server 30 is configured to associate profile information transmitted by kiosk 20 with an arbitrary profile identifier, and is configured to maintain the association of the profile identifier with the profile information in a database. In some embodiments, server 30 is configured to provide a facility for submitting profile information (e.g., a Web form, etc.) that is accessible to kiosk 20. In some such embodiments, server 30 is configured to return a profile identifier to kiosk 20 in response to submitted profile information. In some embodiments, kiosk 20 is be configured to automatically gather and submit profile information to server 30, and server 30 is configured to return a profile identifier to kiosk 20 in response to submitted profile information.

It will be appreciated that kiosks may be configured to obtain a profile identifier by other means.

FIG. 3 is a diagram of a system 100 according to an example embodiment. In system 100, a central server 110 is communicatively coupled with client health kiosks 120 and 140. Client health kiosks 120 and 140 differ in their configurations and logical affiliations, and have correspondingly different profiles.

For instance, kiosk 120 and kiosk 140 differ in the following respects:

Physiological measurement apparatus: Kiosk 120 comprises a first plurality of physiological measurement apparatus 130, which consists of a scale 130A and a heart rate monitor 130B; kiosk 140 comprises a second plurality of physiological measurement apparatus 150, which consists of a portable blood pressure monitor 150A and a blood glucose meter 150B;

User interface apparatus: kiosk 120 comprises a keyboard 134 and mouse 136; kiosk 140 comprises a touch screen display 156;

User identification apparatus: kiosk 120 comprises a barcode scanner 138, which may be used to scan a user identifying barcode; kiosk 140 comprises touch screen display 156, which may be used to key-in user identifying information;

Institution: Kiosk 120 is located in a first care home (not shown); kiosk 140 is located in a second care home (not shown); and Local physical surrounding: Kiosk 120 is located in an exercise area (not shown); kiosk 140 is located in a cafeteria (not shown).

Server 110 is configured to run a Web server and a database server. Kiosk 120 and kiosk 140 are configured to run Web browsers. Kiosk 120 and kiosk 140 are configured to transmit profile information 124 and 144, respectively, and HTTP requests 126 and 146, respectively, to server 110. Web server 112 is configured to provide HTTP responses 116 and 118 to kiosk 120 and kiosk 140, respectively. Responses 116 and 118 each comprise Web content customized for a profile of each of kiosk 120 and kiosk 140, respectively, which server 110 obtains using profile information 124 and 144, respectively. Web content in HTTP responses 116 and 118 is rendered by the Web browsers of kiosks 120 and 140, respectively, to provide user interfaces 128 and 148, respectively, which comprise different display elements.

Figure 4A:
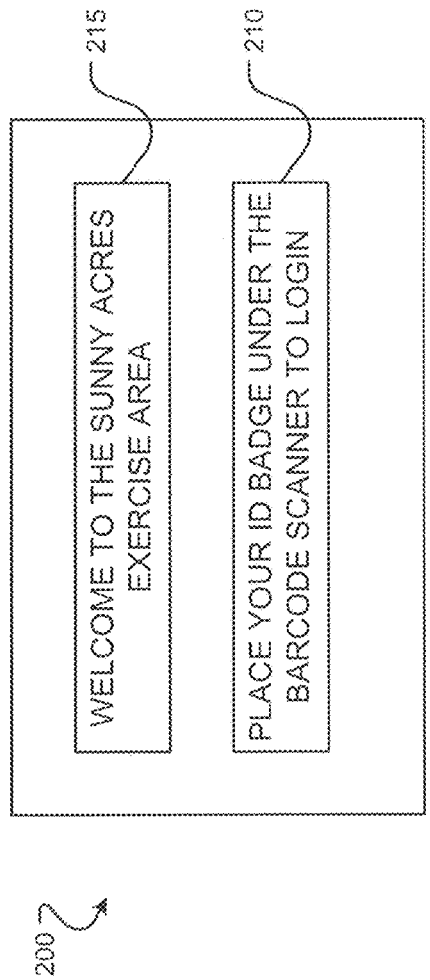
Figure 4B:
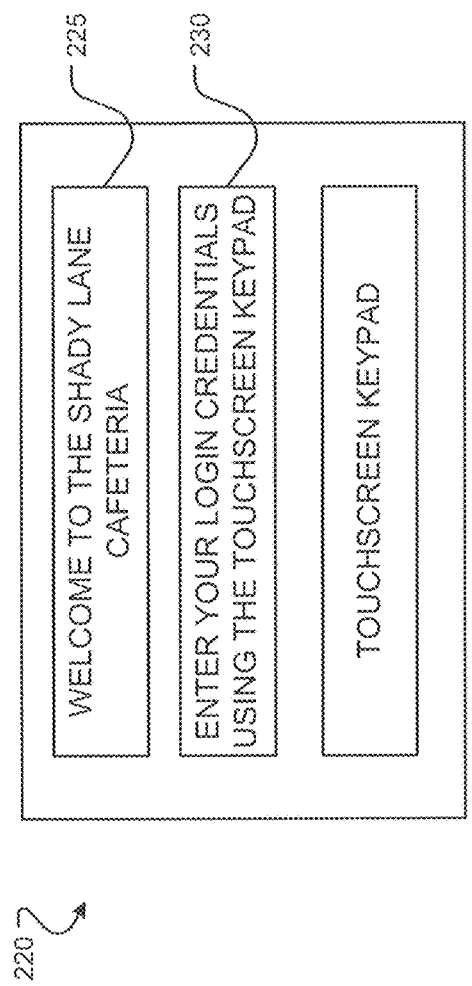

FIG. 4A is a diagram representing a rendering 200 of Web content provided from server 110 to kiosk 120 by the Web browser of kiosk 120. FIG. 4B is a diagram representing a rendering 220 of Web content provided from server 110 to kiosk 140 by the Web browser of kiosk 140. Renderings 200 and 210 are of Web content for a Web page presented before a user logs onto the system. Renderings 200 and 220 differ in that rendering 200 provides a display element corresponding to barcode scanner 138, namely an invitation 210 to login by swiping an identification card through the bar code scanner, whereas rendering 220 provides a display element corresponding to touch screen display 156, namely an invitation 230 to login by entering credential information using the touchscreen interface. Renderings 200 and 220 also differ in that they provide different display elements, 215 and 225, respectively, corresponding to the respective logical affiliations of kiosks 120 and 140. More particularly, display elements 215 and 225 identify their respective kiosks as belonging to their respective care homes and being situated in their respective physical surroundings.

FIG. 5A is a diagram representing a rendering 240 of Web content provided from server 110 to kiosk 120 by the Web browser of kiosk 120. FIG. 5B is a diagram representing a rendering 260 of Web content provided from server 110 to kiosk 140 by the Web browser of kiosk 140. Renderings 240 and 260 are of Web content for a Web page presented after a user logs onto the system. Both renderings 240 and 260 display messages, 253 and 273, respectively, that welcome the user by name. Both renderings 240 and 260 provide the user with controls, 255 and 275, respectively, to view records of past measurements. In some embodiments, controls 255 and 275 are configured to permit users to view records of past measurements obtained at other kiosks (e.g., records of past measurement obtained at kiosk 140 may be viewed at kiosk 120 through operation of control 255).

Renderings 240 and 260 differ in that rendering 240 provides a user with a control 245 for operating a scale and a control 250 for operating a heart rate monitor, whereas rendering 260 provides a user with a control for operating a portable blood pressure monitor 265 and a control for operating a blood glucose meter 270. Renderings 240 and 260 also differ in that each presents information relevant to the particular physical surrounding of kiosks 120 and 140, respectively. More particularly, rendering 240 presents a control 257 that provides the user with the ability to view a schedule of and sign up for exercise classes, and rendering 260 presents a control 277 that provides the user with the ability to view menus for upcoming meals, order food items for upcoming meals and reserve dining times.

In some embodiments, kiosks 120 and 140 are configured to provide profile information 124, 144 to server 110 in HTTP requests 126, 146, and server 110 is configured to provide HTTP responses 116, 118 to kiosks 120 and 140 that contain Web content customized for the particular profiles of kiosks 120 and 140.

In some embodiments, server 110 is configured to host static, profile-specific resources and kiosks 120 and 140 are configured to generate HTTP requests 126, 146 that contain uniform resource locators (URLs) having paths and/or query strings that identify static, profile-specific resources corresponding to the profiles of the client health kiosks 120 and 140. For example, server 110 may be configured so that the Web content it hosts is organized by paths corresponding to different profiles, and kiosks 120 and 140 may be configured to generate HTTP requests 126, 146 that contain URLs having paths corresponding to their respective profiles. Such paths may comprise, at least implicitly, profile information. For example, a path may comprise profile identifiers, configuration information, affiliation information, combinations thereof, and the like.

In some embodiments, Web browsers of kiosks 120 and 140 are configured so that the URL of their default or home pages identify a profile-specific static resource on server 110. In such embodiments, when the Web browsers of kiosks 120 and 140 are initially loaded (e.g., when kiosks 120 and 140 are powered on), the Web content initially provided by server 110 in HTTP responses 116, 118 is customized to the profiles of the kiosks 120 and 140. In such embodiments where kiosks 120 and 140 are configured so that, in typical operation (e.g., without administrator privileges), users may operate kiosks 120 and 140 only through content (e.g., links) provided in Web content displayed in the Web browser, server 110 may be configured so that all Web content navigable from the home page of the Web browsers of kiosks 120 and 140 is customized for the profiles corresponding to the home pages.

In some embodiments, server 110 is configured to generate dynamic, profile-specific resources based on profile information 124, 144 received along with and/or part of HTTP requests 126, 146 from kiosks 120 and 140. For example, server 110 may comprise applications configured to generate Web content customized to the profiles of kiosks 120 and 140 dynamically using a Web application framework, such as, for example, Perl, PHP, Java, Python, Ruby, CFML (ColdFusion), ASP.NET, and the like. HTTP requests from kiosks may comprise URLs that identify such dynamic resources.

In some embodiments, kiosks 120 and 140 are configured to generate HTTP requests 126, 146 that contain URLs having paths and/or query strings corresponding to their respective profiles that identify dynamic resources on server 110, and server 110 is configured to interpret the paths and/or query strings to generate dynamic, profile-specific Web content that it provides to kiosks 120 and 140. Such paths and/or query strings may comprise, at least implicitly, profile information 124, 144. Query strings may be formatted according to a scheme that specifies the pattern or arrangement of data elements that specify profile information 124, 144. Server 110 may be configured to interpret such query strings to extract profile information 124, 144.

In some embodiments, kiosks 120 and 140 are configured to communicate profile information to server 110 using one or more HTTP cookies that contain profile information. As is understood in the art, an HTTP cookie is a piece of text stored by a Web browser that may be transmitted to a Web server as part of an HTTP request and used by the Web server to, for example, track the browsing activity of a Web browser, authenticate a user of the Web browser, store browser-session specific information (e.g., preferences, shopping cart contents), identify a server-based session, and the like. A cookie may comprise of one or more name-value pairs containing bits of information, which may be encrypted for information privacy and data security purposes. For convenience a cookie containing profile information 124, 144 may be referred to herein as a "profile cookie".

In typical operation, cookies are "set" by Web servers on Web browsers. In typical operation a Web server that wishes to store information on at a client Web browser responds to an HTTP request from the browser with an HTTP response packet that has a "Set-Cookies" header field containing a name-value pair chosen by the Web server. The browser, upon receiving the response packet and reading the cookie header field therein, records the Web server's URL as well as the assigned cookie in a (local) data store as a name-value pair (e.g., as a record in a database, as a file in a folder, as an entry in a system registry, etc.). When the browser subsequently generates an HTTP request to a URL that corresponds to the cookie, the browser includes the name-value pair, unchanged, in the "Cookie" header field of the HTTP request. When the Web server receives the HTTP request with the cookie, it will recognize the origin of the request (i.e., the particular Web browser) based on the cookie. Where the Web browsers of kiosks 120 and 140 have a profile cookie associated with the URL of server 110, HTTP requests (such as HTTP requests 126, 146) that the Web browsers of kiosks 120 and 140 send to server 110 will contain a "cookie" header containing profile information.

Multiple profile cookies may be used to communicate different pieces of profile information. In a non-limiting example embodiment, kiosk 120 is configured to communicate a first profile cookie that specifies in a first name-value pair a profile identifier and a second profile cookie that specifies in a second-name value pair a unique identifier for the kiosk. An HTTP request 126 sent by kiosk 120 according to this example might contain the following data:

> Cookie: KioskConfiguration=TouchScreenWithMSCR;
> KioskID=12345678-1234-1234-1234-123456789ABC Where KioskConfiguration and KioskID are names of different values, and TouchScreenwithMSCR and 12345678-1234-1234-1234-123456789ABC are the cookies' respective values.

In some embodiments, a profile cookie contains a single name-value pair, and the value comprises several distinct pieces of profile information. In a non-limiting example embodiment, kiosk 120 is configured to communicate a cookie that specifies, in a name-value pair, several distinct pieces of profile information that are concatenated together. An HTTP request 126 sent by kiosk 120 according to this example might contain the following data:

> Cookie: KioskConfiguration="KioskID=12345678-1234-1234-1234-123456789ABC&KioskScreen=640×480&KioskLoginMethod=BarCodeScanner&KioskUserInput=TouchScreen&KioskLocation=9AC&KioskSensors=tableTopBPCuff,weightScale"

In some embodiments, the Web server of server 110 is configured to provide profile information extracted from cookies to applications running on server 110. For example, the Web server of server 110 may be configured to decompose a cookie containing several distinct pieces of profile information for processing by applications running on the Web server. In an example embodiment in which the Web server of server 110 operates the Microsoft Internet Information Server (MIIS) and the ASP.NET Web application framework, the Web server presents cookie values to the ASP.NET Web application framework, which decomposes the cookie values and provides them to ASP.NET Web applications as a collection attribute of a global Request object, which can be accessed by index or by name.

The ASP.NET framework may be configured to decompose cookies into subitems that it makes available to a receiving Web application. For instance, in such an embodiment the cookie:

> Cookie: KioskConfiguration="KioskID=12345678-1234-1234-1234-Pcuff,weightScalekScreen=640×480&KioskLoginMethod=BarCodeScanner&KioskUserInput=TouchScreen&KioskLocation=9AC&KioskSensors=tableTopBPCuff,weightScale"

might be decomposed into the following subitems:

> KioskID=12345678-1234-1234-1234-123456789ABC
> KioskScreen=640×480
> KioskLoginMethod=BarCodeScanner
> KioskUserInput=TouchScreen
> KioskLocation=9AC
> KioskSensors=tableTopBPCuff,weightScale and the receiving Web application may be configured to generate profile-specific content based at least in part on the profile information received from the ASP.NET Web application framework. Such profile-specific content may then be sent to the particular kiosk from which the cookie was transmitted.

FIG. 6 is a diagram of a system 300 according to an example embodiment. In system 300, a server 310 is communicatively coupled with client health kiosk 320. Server 310 comprises a Web server 312, a profile information extractor 314, and a user database 316. Kiosk 320 comprises a touchscreen 322, no audio support, and a singe physiological measurement apparatus 324 (weight scale 324A) connected as physiological measurement apparatus. Kiosk 320 is configured to transmit an HTTP request 330 to server 310. HTTP request 330 includes a profile cookie 332 and a URL 334. Cookie 332 contains the following profile information, which reflects the configuration aspects and logical affiliations of kiosk 320:

```
KioskID=7fc543a9-3cda-8903-4776-1cd76a459bc2
KioskUserInput=TouchScreen
KioskAudio=no
KioskSensors=weightScale
```

URL 334 identifies a resource at server 310. Profile information extractor 314 is configured to extract profile information from cookie 332. Profile information extractor 314 is configured to interpret the KioskID value as a profile identifier, and to associate it with profile information, such as by a lookup table or the like, for example. In this example embodiment, profile information extractor 314 associates the KioskID value with the name of a care facility where kiosk 320 is located.

Extracted profile information is provided to Web server 312, which generates HTTP response 340 based at least in part on the extracted profile information, for example. HTTP response 340 may comprise Web content that when rendered by the Web browser of kiosk 320 identifies the kiosk as belonging to the care facility where the kiosk is located (based on the KioskID value) and invites users to login by entering their credentials using touch screen keypresses (based the KioskUserinput=TouchScreen profile information).

A user enters her username and password using the touchscreen. Kiosk 320 is configured to send the information entered by the user as a query string in a URL 354 in an HTTP request 350 to server 310 upon the user's command (e.g., pressing a "Login" button). Web server 312 is configured to extract the username and password from the HTTP request and is configured to authenticate the user's credentials using information contained in user database 316. Web server 312 may be configured to limit the username lookup to only those individuals resident at the particular care facility with which kiosk 320 is associated.

After the user's credentials are authenticated, Web server 312 retrieves user information from user database 316, including a user name, an indication that previous weight measurements for the user are available, and an email address for the user. Web server 312 then sends an HTTP response 360, which sets a session cookie 362 that identifies the particular user on kiosk 320. HTTP response 360 also includes Web content that when rendered by the Web browser of kiosk 320 welcomes the user by name (based on the retrieved user name) and presents the user with the options of viewing previous weight measurements (based on retrieved user information indicating the availability of such measurements), emailing previous weight measurements to the user (based on retrieved user information indicating the availability of such measurements and an email address for the user) taking new weight measurements (based on the KioskSensors=weightScale profile information) and viewing tutorials for how to use the scale to take weight measurements (based on the KioskSensors=weightScale profile information). Other aspects of Web content provided by Web server 312 may be based on user information contained in user database 316, such as, for example, language, font size and the like. The user is not presented with options to take measurements using or view tutorials pertaining to other types of physiological measurement apparatus, which are not connected to the kiosk.

If the user chooses to view tutorials for how to use scale 324A, server 310 is configured to provide tutorials that include video with embedded text, rather than video with sound, since the kiosk profile information indicates that there is no sound available (KioskAudio=no).

Server 310 may be configured to set one or more profile cookies on kiosk 320. Server 310 may be configured to set profile cookies based on profile information contained in a HTTP request by the Web browser of kiosk 320. For example, kiosk 320 may be configured to generate an initial HTTP request that contains a path and/or query string corresponding to profile information, and server 310 may be configured to, in response to receiving the HTTP request, transmit to kiosk 320 a HTTP response including a Set-Cookie field that contains one or more profile cookies corresponding to profile information corresponding to the path and/or query string. When it receives the HTTP response, kiosk 320 will set the one or more profile cookies.

In some embodiments, one or more profile cookies stored on kiosk 320 are set locally rather than by server 310. Where profile cookies are set locally on kiosk 320, profile cookies may be sent in HTTP requests to server 310 from the Web browser of kiosk 320 even where server 310 has not previously corresponded with the Web browser.

Kiosk 320 may be configured to set profile cookies locally using any of a variety of techniques. In some embodiments, kiosk 320 is configured to enable profile cookies to be set locally by a manual technique. For example, kiosk 320 may be configured to permit a profile cookie to be set by a technician or locally executing configuration utility during installation.

In some embodiments, kiosk 320 is configured to set one or more profile cookies autonomously. For example, kiosk 320 may be configured to set cookies using a function call, such as a system API function call, for example. For instance, in an embodiment where kiosk 320 is configured to run the Windows CE operating system, kiosk 320 may be configured to set a profile cookie by calling the InternetSet-Cookie/InternetSetCookieEx function provided by the Windows API. In some embodiments, kiosk 320 is configured to run a background process or service configured to make such a cookie-setting function call.

In some embodiments, kiosk 320 is configured to set one or more profile cookies by writing a data structure containing the cookie(s) as they would be stored if they had been set by the browser (e.g., in response to receiving an HTTP response). For instance, in the case of a kiosk 320 configured to run a combination of the Windows CE operating system and the Internet Explorer Web browser, a persistent cookie could be set prior to the launch of the Internet Explorer browser by creating a suitably formatted cookie file within the \Windows\Cookies directory.

In some embodiments, kiosk 320 is configured to run a local "dummy" Web server configured to set a profile cookie when a Web browser running on kiosk 320 makes an HTTP request to the dummy Web server. For example, kiosk 320 could be configured to run a "dummy" Webserver on localhost and be configured to temporarily map the URL of a central server to localhost. A Web browser on kiosk 320 could be configured to make a request to the URL of the central server while that URL is mapped to localhost. As a result of the mapping, the request would be routed to the dummy server running on localhost. The local dummy server would then send a "Set-Cookie" header back in its response, causing the cookie value(s) to be stored in the Web browser's cookie store. Subsequent remapping of the URL to server 310 (e.g., restoration of the natural mapping) will cause subsequent HTTP requests, which include the cookie value(s), to be transmitted to the central server.

In some embodiments, kiosk 320 is configured to maintain profile information in one or more local data stores, and to apply this profile information in generating profile cookies (e.g., by transmitting profile information to a profile cookie-generating server, by inputting the profile information to a local profile cookie-generating process, etc.). Profile information may be added to a local data store manually (e.g., programmed by a technician), autonomously (e.g., by a program that runs at boot-up, by a background process configured to continuously monitor the configuration of kiosk 320, etc.), or through a combination thereof.

In some embodiments, kiosk 320 is configured to obtain profile information and locally set one or more profile cookies containing at least some of the obtained profile information on boot-up. For example, in some embodiments, a kiosk 320 is configured to run the Windows CE operating system and an application is specified in the kiosk's Windows CE system registry HIVE_KEY_LOCAL_MACHINE\init registry key to be launched upon the (re)boot of the kiosk. This application obtains kiosk-specific profile information using sources including without limitation the following:
(a) specific keys and values in the kiosk device's system registry; and
(b) operating system API calls, including:
  (i) GlobalMemoryStatus( ) system call, to determine the overall memory available to the kiosk;
  (ii) GetSystemInfo( ) system call, to determine the processor architecture, level and revision, and to determine what platform-dependent code can run on the kiosk;
  (iii) QueryInstructionSet( ) system call, to determine the level of CPU instruction support for a particular processor;
  (iv) IsProcessorFeaturePresent( ) system call, to determine whether or not floating point operations are emulated; and
  (v) GetVersionEx( ) system call, to determine the major/minor/build numbers of the operating system.

After obtaining kiosk-specific profile information, the application sets one or more profile cookies using the InternetSetCookie system call. After setting the profile cookie(s), the application launches the Internet Explorer browser application. It will be appreciated that in this embodiment, it is ensured that the current profile of the kiosk is reflected in the cookie store prior to the first HTTP request to server 310.

In some embodiments, kiosk 320 is configured to continually monitor one or more sources of profile information for changes, and to transmit updated profile information to server 310 when profile information changes. For example, kiosk 320 may be configured to run a background process, such as, for example, a system service, daemon or the like, that monitors device interfaces (e.g., Plug and Play™ events) and network interfaces of kiosk 320, and to set one or more profile cookies (e.g., set a new profile cookie and/or update the value of a previously set profile cookie) when devices are added or removed at the device interfaces or network interfaces. The new and/or updated profile cookie will be transmitted to server 310 in subsequent HTTP requests directed to server 310. In some embodiments where kiosk 320 is configured to run the Windows CE operating system, kiosk 320 is configured to monitor one or more sources of profile information using a dynamic link library hosted within the services.exe process, for example. In addition to monitoring and obtaining profile information, such a dynamic link library may be configured to set one or more profile cookies. It will be appreciated that by updating profile cookies in response to the discovery of devices, different Web content (e.g., menu options, tutorials, etc.) may be provided by and/or made available by server 310 to kiosk 320.

Non-profile cookies may be used in generating Web content for kiosk 320. For example, Web server 312 may set session cookies to maintain state information for a current user session established between a particular kiosk 320 and server 310. For example, session cookies may be used to track the identity of a user of kiosk 320, and to provide content customized to the particular user (e.g., display preferences, records of past physiological measurements, etc.).

Information contained in profile cookies may be used by server 310 for purposes other than generating Web content for kiosk 320. In some embodiments, server 310 is configured to provide information contained in profile cookies to administrators through an administrative interface (e.g., a Web page served by server 310 at a particular URL). In some embodiments, server 310 is configured to monitor certain profile cookies and/or values thereof, and to trigger actions based on observed particular profile cookies and/or values thereof. For example, kiosk 320 may be configured to periodically perform diagnostic tests on attached physiological measurement apparatus 324 and to update a profile cookie containing an indication of the results of the diagnostic tests, and server 310 may be configured monitor the profile cookie and to dispatch an email message to administrative staff of the facility with which kiosk 320 is associated when the results of the diagnostic test indicate that corrective action is required. For instance, kiosk 320 may be configured to periodically check a battery power level of a physiological measurement apparatus 324 connected to kiosk 320 (which kiosk 320 is configured to obtain from the apparatus), and to update a profile cookie to indicate the current battery power level; server 310 may be configured to periodically monitor the profile cookie and to dispatch an email message to administrative staff of the facility with which kiosk 320 is associated when the battery power level is below a threshold.

It will be appreciated that periodic diagnostic testing and reporting the results of same to server 310 may be applied to ensure that faults occurring at kiosk 320 and physiological measurement apparatus 324 connected thereto may be detected and remedied expediently. In some embodiments, results of diagnostic tests are stored for auditing purposes. Server 310 may be configured to digitally sign results of diagnostic tests. It will be appreciated that results of periodic diagnostic tests may be communicated to server 310 by means other than profile cookies (e.g., uploaded as a text file via FTP, entered as an HTTP POST submission, etc.)

Physiological measurement apparatus 324 and other peripherals connectable to kiosk 320 may require configuration parameters and/or software components, such as device drivers, authentication modules, and the like, in order to be used with kiosk 320. Required configuration parameters and software components may be device specific and/or kiosk configuration specific (e.g., enabling a particular physiological apparatus to be used with a kiosk having a particular operating system may require a specific software component). Kiosk 320 may be configured to cooperatively manage connections with attached physiological measurement apparatus 324 and may be configured to dynamically configure connections with attached physiological measurement apparatus 324 for interaction with kiosk 320. In some embodiments, kiosk 320 may be configured to obtain configuration parameters and/or software components for configuring connections with attached physiological measurement apparatus 324 from server 310.

In an example embodiment, kiosk 320 is configured to continually monitor device interfaces (e.g., for Plug and Play™ events) and network interfaces of kiosk 320 for physiological measurement apparatus 324 that have been plugged into (or removed from) the system or are requesting connection to the system (such as by wireless link, for example), and to notify server 310 of any apparatus 324 newly discovered by kiosk 320. Kiosk 320 may be configured to collect identifying information about physiological measurement apparatus 324 connected to, or seeking connection with, kiosk 320, and to communicate such identifying information to server 310. Identifying information may comprise an identification of the manufacturer of the device, the device type and model, firmware revision, device serial numbers, and the like. For example, in the case of a USB device, kiosk 320 may be configured to collect information such as the device's manufacturer ID, its product ID, its version number, and its supported data/control channels and their class, subclass and protocol types. For another example, in the case of a Bluetooth device, kiosk 320 may be configured to collect information such as the device's Bluetooth address, its device name, its Class Of Device (COD), and its protocol form. Other identifying information may be collected for the aforementioned device types and for other device types.

Kiosk 320 may be configured to notify server 310 of newly discovered physiological measurement apparatus 324 by sending an HTTP request to server 310, by locally modifying one or more existing profile cookies, and/or by locally setting one or more new profile cookies, for example.

In some embodiments, server 310 is configured to provide configuration parameters and/or software components to kiosk 320 for configuring connections with attached physiological measurement apparatus 324 from server 310 in response to receiving notification of devices newly discovered by kiosk 320 (e.g., notifications in the form of an HTTP request containing a particular URL, an HTTP request containing modified profile cookie value(s), an HTTP request containing a new profile cookie, etc.). Server 310 may be configured to determine configuration parameter(s) and/or software component(s) to be provided to kiosk 320 based on identifying information about the device and/or configuration information pertaining to kiosk 320, using a lookup table or the like, for example. Software components provided by server 310 may include, for example, software components for authenticating the device, drivers for interfacing with the device, dynamic link libraries (DLLs) for facilitating the filtering, translating and transcoding of the measurement data from physiological measurement apparatus 324, and the like. Server 310 may be configured to provide configuration parameters and/or software components to kiosk 320 in the form of an HTTP response. Server 310 may be configured to obtain configuration parameters and/or software components from a local store or from a remote store (e.g., a server maintained by a device manufacturer, etc.).

In some embodiments, kiosk 320 is configured to install software components received from server 310 and to apply configuration parameters received from server 310 to configure connections with the relevant physiological measurement apparatus. Received software components may be installed in persistent storage accessible to kiosk 320.

In embodiments where customized Web content is provided to kiosks from a server, content provided to kiosks may be determined by the configuration of the server. In such embodiments, the content provided to a group of kiosks having a common profile may be determined by a common configuration that is centrally administered at the server. In some embodiments, a server is configured to provide an interface at which an administrator (e.g., an employee of a health care facility) can manage the configuration of the server. For example, a server may be configured to provide an interface at which an administrator can specify aspects of the Web content that is to be provided to kiosks having particular profiles. Such an interface may enable an administrator to efficiently customize the "look and feel" of a number of kiosks having common profiles. A server may provide an interface for specifying aspects of Web content including without limitation:
  advertisements;
  affiliation information (e.g., a logo identifying the facility where the
  kiosk is located);
  announcements (e.g., of events of interest to users resident in the facility where the kiosk is located); and
  the like.

In some embodiments, a server is configured to provide an interface at which an administrator can ascertain the operational status of kiosks administered by the server (e.g., presence of and/or types of physiological measurement apparatus connected thereto, etc.).

In some embodiments, a server is configured to provide access to a configuration interface via a Web page. Access to the Web page may restricted by user name and password, and/or other security measures. A server may be configured to provide administrative access to a particular administrator only in respect of a subset of kiosks served by the server (e.g., an administrator might only be able to configure the server in respect of its interaction with kiosks that belong to facilities with which the administrator is associated).

Centralized administration of kiosks by a server may be used to provide a facility for obtaining, centralizing and tracking user information. In some embodiments, a server is configured to access and/or maintain a repository of user information. User information maintained by a server may comprise, for example:
  physiological measurements collected at kiosks;
  kiosk use information (e.g., times of instances of use, durations of user activities undertaken at kiosks, etc.);
  personal information (e.g., age, gender, address and contact information);
  health information (e.g., prescribed medications, health conditions, treatment histories, physiological measurements, etc.);
  dietary restrictions;
  health provider information (e.g., names and contact information for physicians, care aides, case-managers, insurer, etc.);
  friend and relative information (e.g., names and contact information for physicians, care aides, case-managers, insurer, etc.);
  user interface preferences (e.g., language, font size, etc.)
  membership information (e.g., in clubs, support groups, etc.); and
  preferences for food, entertainment etc; and
  the like.

In some embodiments, a server is configured to store physiological measurement data according to standard formats, such as HL7-compliant electronic medical records (EMRs) or some other suitable standard. A server may be configured to store such records locally in an Open Database Connectivit (ODBC)-compliant 3rd party database for future transfer and/or to transmit such records to an external EMR management system (e.g. hospital or health authority).

In some embodiments, a server is configured to generate Web content for a kiosk actively being used by a user based on the user's user information. For example, a server may be configured to set a session cookie on a kiosk that identifies the current user of the kiosk, and to use the session cookie to obtain user information for use in generating Web content customized to the current user's preferences. In some embodiments, a server is configured to store user information in session cookies to obviate the need for continually accessing user information from the datastore when generating Web content.

In some embodiments, a server is configured to diagnose health conditions, recognize symptoms of health conditions, and the like based on user information. For example, a server may be configured to diagnose health conditions by testing physiological measurements and other health information against one or more rules. A server may be configured to generate alerts (e.g., email or SMS message to health care providers, etc.) upon diagnosing a health condition or the like. A server may be configured to digitally sign diagnoses of health conditions for accountability purposes.

In some embodiments, a kiosk may be configured to analyze physiological measurements (e.g., for purposes of diagnosing conditions, identifying patterns in physiological measurements, etc.). For example, a kiosk may comprise analysis apparatus (e.g., connected via a device interface of the kiosk's computing unit) or analysis software installed on the kiosk's computing unit, or the like. The kiosk may be configured to analyze physiological measurements obtained from connected physiological measurement apparatus and/or obtained from a server to the analysis apparatus (e.g., by providing such measurements to analysis apparatus, analysis software, or the like).

In some embodiments, a server is configured to make user information available to physicians and/or other medical professionals for use by the physician and/or other medical professionals in diagnosing health conditions etc. A server may be configured to provide user information on an anonymous basis (i.e., without personally identifying information). A server may be configured to receive diagnoses from physicians and/or other medical professionals, and to present these diagnoses to kiosk users. A server may be configured to digitally sign diagnoses with private keys of the person making the diagnosis for accountability purposes.

In some embodiments, a server is configured to provide Web content that motivates users to undergo physiological measurements using kiosks. In some embodiments, a server is configured to provide Web content that when rendered by a kiosk offers users inducements to motivate them to undergo physiological measurements. In some such embodiments, the nature of inducements and the conditions of their offer may be based on user information. For instance, in an example embodiment, a user known to have high blood pressure may be motivated to take frequent blood pressure measurements by being offered a discount coupon for the co-payment on his blood pressure medication (as opposed to bags of potato chips, for example) on the condition that he uses a kiosk to take his blood pressure measurement at least twice per day, every day for one week. Other non-limiting example inducements that a server may be configured to offer via a kiosk include:

encouraging messages;
    prizes (e.g., cash, discount coupons, gift certificates, valuable articles, etc.);
    privileges (e.g., privilege of access to certain resources (TV, books, magazines etc.), privilege of reserving spaces at mealtimes, on field trips, in activities, etc., privilege of selecting menu choices, television programs, magazine subscriptions, etc., and the like);
    entry into raffles/lotteries for prizes, privileges etc.;
    peer recognition; and
    the like.

Non-limiting example conditions that a server may be configured to place on offers of inducements made via a kiosk include:

undergoing particular physiological measurements;
    undergoing particular physiological measurements with particular frequency;
    undergoing particular physiological measurements at certain times (e.g., for meals, after meals, before certain meals (e.g., breakfast));
    undergoing physiological measurements at particular kiosks; and
    the like.

In some embodiments, a server is configured to provide an administrative interface at which the nature of inducements and the conditions of their offer may be set manually.

In some embodiments, a server is configured to provide an interface at which third parties (e.g., parties not responsible for the administration of a care facility) may provide inducements and/or conditions on the offer thereof. For example, a server may be configured to provide an interface configured to permit merchants to enter inducements in the form coupons, gift certificates and the like, and specify conditions for their offer (such as characteristics of a particular target audience of kiosk users, expiry date, etc.). In some embodiments, an interface at which third parties may provide inducements and/or conditions on the offer thereof permits third parties to define target audiences for inducements in terms of aspects of user information (e.g., gender, age, inducement preferences, etc.) and/or kiosk profile information (e.g., geographic location, local surroundings, particular facility). Inducements and associated conditions entered by third parties may be subject to approval by an administrator before being presented to kiosk users. Conditions on the offer of inducements entered by third parties may be supplemented by additional conditions entered by an administrator and/or determined by the server.

In some embodiments, a server is configured to determine the nature of inducements and the conditions of their offer based on user information and a set of available inducements, such as according to an algorithm, a lookup table, or the like. In some embodiments, a server is configured to maximize participation in a health monitoring program by optimally motivating a population of users to use kiosks given a limited set of inducements. Conditions on the offer of inducements in a health monitoring program may be set by a server automatically, or with assistance from the administrator of the facility, based on user information. Non-limiting examples of particular conditions on the offer of inducements that may be included in health monitoring programs include the following:

a user taking a blood pressure reading and body weight for the first time;
    a user taking blood pressure reading twice a day (e.g., once in the morning and once in the afternoon) and a body weight reading at least once a day for five consecutive days for the first time;
    a user taking blood pressure reading twice a day and a weight reading at least once a day for five consecutive days;
    a user exhibiting consistent high blood pressure (through readings taken regularly over several days) managing to bring blood pressure within a normal range (observed through readings taken regularly over several days); and a user who was overweight managing to reduce his weight by 10 pounds (again observed through regular use of the system).

In some embodiments, a server is be configured to ration inducements among users who meet conditions on the offer of inducements based on the supply of inducements. In some embodiments, a server is configured to determine which inducements are relatively more attractive to specific users. In one example embodiment, a server is configured to distribute inducements equally (in terms of discrete numbers or value) to users on the basis of participation in a health monitoring program over time, but to distribute relatively more inducements to new users when they initially begin participating in the health monitoring program. This example embodiment may encourage new users to join the program while ensuring that over long term, the users who use the system regularly obtain more inducements than users who use the system intermittently.

Some embodiments described herein may be configured to implement one or more of the following example incentive programs.

HEALTH CLUB—Within a provider network (e.g., one or more facilities managed by a common entity) one or more health clubs are established, with each health club consisting of two or more individuals who have created accounts with the system. Individuals within a particular health club are able to view the physiological measurements of fellow health club members, and able to track each other's progress over time. Individuals who do not belong to a health club are not able to view the physiological measurements of health club members. Health clubs may establish rewards for their members and determine how those rewards would be earned and redeemed. For instance, a group of elderly women in a facility may get together to establish a health club. These women agree to track their blood pressure by taking readings twice a week. Those individuals who fail to measure their blood pressure twice in a week would be ineligible to earn a reward. For the remaining individuals, they may decide to set up the health club so that the system randomly rewards one of the eligible participants with a coupon to a neighbourhood coffee shop once a week. Alternatively, they may decide to set up individualized blood pressure targets, which a participant must meet in order to qualify for the rewards.

LOTTERY—Within a provider network an inducement pool is established, advertised via kiosks and distributed based on use. An example operation of a lottery comprises the following steps:

The staff member of the provider network logs into the server 30 and enters details of the lottery (e.g., inducement information, eligibility criteria, duration, participating kiosks) into a database.

When a kiosk requests its default Web page, its profile cookie is sent to a server.

The server consults the database to determine the lottery details pertaining to the kiosk. Based upon this information, the server generates Web content that when rendered by the kiosk presents a login screen that announces the current lottery details and invites users to participate in the lottery. The announcement may communicate the current odds of winning based on the number of participants to motivate others to join in.

A user logs into the kiosk and takes a blood pressure reading, then logs out. The server records the fact that the user has performed an action that counts towards prize eligibility. The server determines whether the user has met the lottery eligibility criteria (e.g., taking blood pressure twice each day for a week). If the user has met the lottery eligibility criteria, the server enters the user in the lottery. In some embodiments, the server is configured to issue (e.g., causes a printer attached to the kiosk to print, emails to the user, etc.) a ticket to the user. The user may be asked if he/she wishes to participate in the draw before he/she is entered into the lottery and/or issued a ticket.

The server may be configured to randomly select an entry at a pre-determined draw time, and to announce the winner (e.g., generates Web content that when rendered by the kiosk presents a login screen that announces the winner).

VOTING—Within a community (e.g., a single facility) users are allocated votes on a choice based on kiosk use. Potential subjects for voting include: media played on communal AV equipment (music, movies), selection of field trips, facility programming (classes etc.), food choice (e.g., dessert selection), books to be purchased for library, magazines/newspapers to subscribe to, and the like. Votes may be allocated based on a lottery system, such as the one described above (e.g., a vote may be an inducement—where a limited numbers of votes are distributed among kiosk users this may make it more important to an individual that he increase his odds of getting a vote). An example operation of a voting incentive program comprises the following steps:

The staff member of the community logs into a server and enters the details for the vote (e.g., vote subject, eligibility criteria, duration, participating kiosks, etc.)

When a kiosk requests its default Web page, its profile cookie is sent to the server.

The server consults the database to determine the voting details pertaining to the kiosk. Based upon this information, the server generates Web content that when rendered by the kiosk presents a login screen that announces the current voting details and invites users to participate in voting. The announcement may communicate the current vote totals to motivate participation.

A user logs into the kiosk and takes a blood pressure reading. The server recognizes that the user is eligible to vote on the vote subject. The server generates Web content that when rendered by the kiosk presents a voting screen to the user. The user makes his/her vote at the kiosk, and the vote is transmitted to the server, which records the vote.

The server may be configured to close voting at a particular time, count the votes and to announce the winning choice.

RESERVATIONS—Within a facility, users may be privileged with access to scarce resources on the basis of kiosk use. Potential resources subject to reservation include: time slots for services/activities (bath times, massages, dining), spaces in limited capacity activities (field trips, classes, etc.), choices of food (e.g., pie or pudding for dessert), temporary custody of physical objects (books, magazines, etc.), and the like. Resources may be made artificially scarce (e.g., 10 servings of pie versus 190 servings of pudding).

REWARDS—Rewards include coupons and gift certificates, which can be coordinated with the facility's advertising strategy. Rewards may be transferable (e.g., sent to non-resident acquaintances).

A third party vendor logs into a server, uploads an image file of a coupon and specifies the details of the coupon offer (e.g., maximum number of coupons to be issued, time period in which to issue coupons, offer target audience (in terms of kiosk profile information and/or user profile information, such as geographic region, facility, local surrounding, age, gender, and the like)).

The server generates unique coupon identifiers (e.g., barcodes) and adds the ids to the list of coupons issued by the vendor.

The server searches the user database for users belonging to the offer target audience (e.g., those users of a certain gender who have used kiosks in a particular geographic region) and emails coupons to those users.

It will be appreciated that features of two or more of the above incentive programs may be combined.

It will be appreciated that embodiments disclosed herein may be modified and/or supplemented in many ways, such as, for example:

A server may be configured to access a datastore comprising scheduling information associated with users, and to provide Web content that when rendered by a kiosk presents a user with a reminder of an event or task in the user's schedule (e.g., a reminder to take a particular medicine, a reminder of an upcoming appointment, etc.)

A server may be configured to provide Web content that when rendered by a kiosk presents a user with an advertisement. Advertisements may be selected based on kiosk profile information, user information or a combination thereof, for example. Advertisements may be selected using an algorithm, a lookup table, or the like.

A server may be configured to provide user information and/or kiosk profile information to a third-party content provider (e.g., advertising network), and to provide Web content comprising content provided by the third-party content provider (e.g., advertisements targeted to a particular kiosk and/or user).

A kiosk may comprise a plurality of displays, and the computing unit of the kiosk may be configured to run a corresponding plurality of different web browser sessions. User input apparatus corresponding to each display/browser session may be provided. Physiological measurement apparatus of the kiosk may be shared among the browser sessions.

Where a component (e.g. a kiosk, server, computing unit, physiological measurement apparatus, display, user identification apparatus, user interface apparatus, web browser, web server, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

It will be appreciated that where aspects of configuration and/or functionality are ascribed to components, such aspects of configuration and/or functionality may be embodied or implemented in the configuration and/or functionality of one or more sub-components or combinations therefor. Accordingly, descriptions of configuration and/or functionality of components herein should be construed as describing corresponding configuration and/or functionality of sub-components as applicable. For example, a description of a kiosk as being configured to perform particular actions or having particular characteristics, should be understood as also describing the configuration and characteristics of the computing unit of the kiosk and of the web browser of the kiosk and computing unit.

Aspects of the invention may be provided in the form of a program product. The program product may comprise any non-transitory medium which carries a set of computer-readable information comprising instructions which, when executed by a data processor, cause the data processor to execute a method of the invention. Program products according to the invention may be in any of a wide variety of forms. The program product may comprise, for example, physical media such as magnetic data storage media including floppy diskettes, hard disk drives, optical data storage media including CD ROMs, DVDs, electronic data storage media including ROMs, flash RAM, or the like. The computer-readable information on the program product may optionally be compressed or encrypted.

Those skilled in the art will appreciate that embodiments described herein may be practised or implemented without all of the features ascribed to them herein, and that certain features of embodiments described herein may be used in combination with features of other embodiments described herein. Method embodiments may include features that correspond to features of apparatus embodiments described herein, and vice versa. Such variations on described embodiments that would be apparent to the skilled addressee, including variations comprising mixing and matching of features from different embodiments, are within the scope of this invention.

As will be apparent to those skilled in the art in the light of the foregoing disclosure, many alterations, modifications, additions and permutations are possible in the practice of this invention without departing from the spirit or scope thereof. The embodiments described herein are only examples. Other example embodiments may be obtained, without limitation, by combining features of the disclosed embodiments, by re-arranging the components of disclosed embodiments, and/or by re-ordering the operations of disclosed embodiments.

What is claimed is:

1. A method of digitally signing a physiological measurement of a health kiosk comprising a computing unit and at least one physiological measurement apparatus, the method comprising:

transmitting, from a Web browser at the kiosk to a server, profile information of the kiosk in the form of an HTTP request comprising an HTTP cookie stored in a memory of the computing unit, the profile information comprising a configuration selection from among a plurality of possible configurations of the at least one physiological measurement apparatus, the at least one physiological measurement apparatus operatively connectable to a human user for measuring a physiological characteristic of the user and the at least one physiological measurement apparatus configurable to measure and output one or more physiological measurements of the physiological characteristic based on the configuration selection;

transmitting from the kiosk to the server a request for a resource; and in response to receiving the profile information and the request:

generating dynamic, profile-specific, client-side executable Web content configured to run on the Web browser, responsive to the request and based at least in part on the profile information, the dynamic, profile-specific, client-side executable Web content comprising:
a first and a second display element,
the first display element, when rendered by the Web browser by executing the dynamic, profile-specific, client-side executable Web content, provides a user interface based on the configuration selection for user control, locally at the kiosk via the Web browser and the user interface, of the at least one physiological measurement apparatus to measure and output the one or more physiological characteristic, and
the second display element, when rendered by the Web browser, provides a data display element for displaying data output by the at least one physiological measurement apparatus locally at the kiosk via the Web browser and the user interface;
transmitting from the server to the kiosk the dynamic, profile-specific, client-side executable Web content;
rendering, by the Web browser, the dynamic, profile-specific, client-side executable Web content on a display at the kiosk by executing the dynamic, profile-specific, client-side executable Web content;
receiving, by the user interface of the first display element, a user identifier and a password from the user;
generating, by the kiosk, a password hash from the password;
transmitting, by the kiosk, the user identifier and the password hash to the server;
verifying, by the server, the password hash by comparing the password hash to a stored password hash associated with the user identifier;
transmitting, by the server, an encrypted private key associated with the user identifier to the kiosk;
generating, by the kiosk, a secret key from the password;
decrypting, by the kiosk, the encrypted private key with the secret key to generate a decrypted private key;
measuring the one or more physiological characteristic with the at least one physiological measurement apparatus of the kiosk;
generating, by the kiosk, a first verification hash of the physiological measurement;
encrypting, by the kiosk, the first verification hash with the decrypted private key to generate a first encrypted verification hash; and
transmitting, by the kiosk, the physiological measurement and the first encrypted verification hash to the server.

2. The method of claim 1, comprising:
receiving, by the kiosk, the physiological measurement, the first encrypted verification hash, and a public key paired with the decrypted private key from the server;
decrypting, by the kiosk, the first encrypted verification hash with the public key to generate a first decrypted verification hash;
generating, by the kiosk, a second verification hash from the physiological measurement;
encrypting, by the kiosk, the second verification hash with the decrypted private key to generate a second encrypted verification hash;
decrypting, by the kiosk, the second encrypted verification hash with the public key to generate a second decrypted verification hash;
verifying, by the kiosk, the first decrypted verification hash by comparing the first decrypted verification hash to the second decrypted verification hash; and
displaying, by the second display element, the physiological measurement.

3. The method of claim 2, comprising:
generating, by the kiosk, the decrypted private key and the public key;
encrypting, by the kiosk, the decrypted private key with the secret key to generate the encrypted private key;
receiving, by the user interface of the first display element, user information from the user;
encrypting, by the kiosk, the user information with the secret key to generate encrypted user information;
transmitting, by the kiosk, the public key, encrypted user information and the encrypted private key to the server; and
storing, by the server, the public key, the encrypted user information, and the encrypted private key.

4. The method of claim 3 wherein the user information comprises one or more of: a user name, contact information, an age, and a gender.

5. The method of claim 2, comprising:
generating, by the kiosk, corroborative information associated with the physiological measurement;
generating, by the kiosk, a first corroborative information hash from the corroborative information;
encrypting, by the kiosk, the first corroborative information hash with the decrypted private key to generate a first encrypted corroborative information hash;
transmitting, by the kiosk, the corroborative information and the first encrypted corroborative information hash to the server; and
storing, by the server, the corroborative information and the first encrypted corroborative information hash.

6. The method of claim 5, comprising:
transmitting, by the server, the corroborative information and the first encrypted corroborative information hash to the kiosk;
decrypting, by the kiosk, the first encrypted corroborative information hash with the public key to generate a first decrypted corroborative information hash;
generating, by the kiosk, a second verification hash from the corroborative information;
encrypting, by the kiosk, the second verification hash with the decrypted private key to generate a second encrypted verification hash;
decrypting, by the kiosk, the second encrypted verification hash with the public key to generate a second decrypted verification hash;
verifying, by the kiosk, the first decrypted verification hash by comparing the first decrypted verification hash to the second decrypted verification hash; and
displaying, by the second display element, the corroborative information.

7. The method of claim 6 wherein the corroborative information comprises one or more of:
a kiosk identifier identifying the kiosk;
a measurement apparatus identifier identifying the physiological measurement apparatus;
a timestamp of when the physiological measurement was taken by the physiological measurement apparatus;
a timestamp of when the user logged into the kiosk; and
a timestamp of when the user logged out of the kiosk.

8. The method of claim 1, comprising:
encrypting, by the kiosk, the physiological measurement with the decrypted private key to generate an encrypted physiological measurement; and
wherein transmitting, by the kiosk, the physiological measurement to the server comprises transmitting the encrypted physiological measurement to the server.

9. The method of claim 8, comprising:
transmitting, by the server, a public key paired with the decrypted private key, the encrypted physiological measurement and the first encrypted verification hash to the kiosk;
decrypting, by the kiosk, the encrypted physiological measurement with the public key to generate a decrypted physiological measurement;
decrypting, by the kiosk, the first encrypted verification hash with the public key to generate a first decrypted verification hash;
generating, by the kiosk, a second verification hash from the decrypted physiological measurement;
encrypting, by the kiosk, the second verification hash with the decrypted private key to generate a second encrypted verification hash;
decrypting, by the kiosk, the second encrypted verification hash with the public key to generate a second decrypted verification hash; and
verifying, by the kiosk, the first decrypted verification hash by comparing the first decrypted verification hash to the second decrypted verification hash.

10. The method of claim 1 wherein the user identifier comprises an identifier associated with a user name, a barcode, an RFID, or a biometric measurement.

11. A health kiosk system comprising:
a server having a web server; and
a kiosk communicatively coupled to the server, the kiosk comprising:
a computing unit;
a web browser;
a display; and
at least one physiological measurement apparatus connected to the computing unit and operatively connectable to a human user for measuring a physiological characteristic of the user;
wherein the computing unit is configured to:
transmit profile information of the kiosk to the server in the form of an HTTP request comprising an HTTP cookie stored in a memory of the computing unit, the profile information comprising a configuration selection from among a plurality of possible configurations of the at least one physiological measurement apparatus, the at least one physiological measurement apparatus configurable to measure and output one or more physiological measurements of the physiological characteristic based on the configuration selection;
transmit a request for a resource to the server, and
wherein the server is configured to, in response to receiving the profile information and the request:
generate dynamic, profile-specific, client-side executable Web content configured to run on the Web browser, responsive to the request and based at least in part on the configuration selection, the dynamic, profile-specific, client-side executable Web content comprising:
a first and a second display element, the first display element, when rendered by the Web browser by executing the dynamic, profile-specific, client-side executable Web content, provides a user interface based on the configuration selection for user control, locally at the kiosk via the Web browser and the user interface, of the at least one physiological measurement apparatus to measure and output the one or more physiological measurements of the physiological characteristic, and the second display element when rendered by the Web browser, provides a data display element for displaying data output by the at least one physiological measurement apparatus locally at the kiosk via the Web browser and the user interface; and
transmit to the kiosk the dynamic, profile-specific, client-side executable Web content;
wherein the computing unit is operable to cause the Web browser to execute the dynamic, profile-specific, client-side executable Web content and to thereby cause the display to display the first and second display elements including the user interface based on the configuration selection and the data output by the at least one physiological measurement apparatus to thereby permit user control, locally at the kiosk via the Web browser and the user interface, of the at least one physiological measurement apparatus in accordance with the configuration selection; and
wherein the computing unit is further configured to:
receive by the user interface a user identifier and a password from the user;
generate a password hash from the password;
transmit the user identifier and the password hash to the server;
receive from the server an encrypted private key associated with the user identifier;
generate a secret key from the password;
decrypt the encrypted private key with the secret key to generate a decrypted private key;
measure the one or more physiological characteristic with the at least one physiological measurement apparatus;
generate a first verification hash of the physiological measurement;
encrypt the first verification hash with the decrypted private key to generate a first encrypted verification hash; and
transmit the physiological measurement and the first encrypted verification hash to the server.

12. The system of claim 11, wherein the computing unit is further configured to:
receive the physiological measurement, the first encrypted verification hash, and a public key paired with the decrypted private key from the server;
decrypt the first encrypted verification hash with the public key to generate a first decrypted verification hash;
generate a second verification hash from the physiological measurement;
encrypt the second verification hash with the decrypted private key to generate a second encrypted verification hash;
decrypt the second encrypted verification hash with the public key to generate a second decrypted verification hash;
verify the first decrypted verification hash by comparing the first decrypted verification hash to the second decrypted verification hash; and
display the physiological measurement via the second display element.

13. The system of claim 12, wherein the computing unit is further configured to:
generate the decrypted private key and the public key;
encrypt the decrypted private key with the secret key to generate the encrypted private key;

receive, by the user interface, user information from the user;

encrypt the user information with the secret key to generate encrypted user information; and transmit the public key, encrypted user information and the encrypted private key to the server.

14. The system of claim 13, wherein the computing unit is further configured to:

encrypt the physiological measurement with the decrypted private key to generate an encrypted physiological measurement; and wherein transmitting the physiological measurement to the server comprises transmitting the encrypted physiological measurement to the server.

15. The system of claim 14, wherein the computing unit is further configured to:

receive from the server a public key paired with the decrypted private key, the encrypted physiological measurement and the first encrypted verification hash;

decrypt the encrypted physiological measurement with the public key to generate a decrypted physiological measurement;

decrypt the first encrypted verification hash with the public key to generate a first decrypted verification hash;

generate a second verification hash from the decrypted physiological measurement;

encrypt the second verification hash with the decrypted private key to generate a second encrypted verification hash;

decrypt the second encrypted verification hash with the public key to generate a second decrypted verification hash; and verify the first decrypted verification hash by comparing the first decrypted verification hash to the second decrypted verification hash.

16. The system of claim 13 wherein the user information comprises one or more of: a user name, contact information, an age, and a gender.

17. The system of claim 12, wherein the computing unit is further configured to:

generate corroborative information associated with the physiological measurement;

generate a first corroborative information hash from the corroborative information;

encrypt the first corroborative information hash with the decrypted private key to generate a first encrypted corroborative information hash; and transmit the first encrypted corroborative information hash and the corroborative information to the server.

18. The system of claim 17, wherein the computing unit is further configured to:

receive from the server the first encrypted corroborative information hash and the corroborative information;

decrypt the first encrypted corroborative information hash with the public key to generate a first decrypted corroborative information hash;

generate a second verification hash from the corroborative information;

encrypt the second verification hash with the decrypted private key to generate a second encrypted verification hash;

decrypt the second encrypted verification hash with the public key to generate a second decrypted verification hash;

verify the first decrypted verification hash by comparing the first decrypted verification hash to the second decrypted verification hash; and display the corroborative information via the second display element.

19. The system of claim 18 wherein the corroborative information comprises one or more of:

a kiosk identifier identifying the kiosk;

a measurement apparatus identifier identifying the physiological measurement apparatus;

a timestamp of when the physiological measurement was taken by the physiological measurement apparatus;

a timestamp of when the user logged into the kiosk; and a timestamp of when the user logged out of the kiosk.

20. The system of claim 11 wherein the user identifier uniquely identifies a user name, a barcode, an RFID, or a biometric measurement.

* * * * *